US012793223B2

(12) United States Patent
Won et al.

(10) Patent No.: US 12,793,223 B2
(45) Date of Patent: Nov. 10, 2026

(54) METHOD AND ELECTRONIC DEVICE FOR GENERATING 3-DIMENSIONAL BLOOD VESSEL PROFILE DATA

(71) Applicant: Medipixel, Inc., Seoul (KR)

(72) Inventors: Donghyun Won, Seoul (KR); Hyun-Woo Kim, Seoul (KR)

(73) Assignee: Medipixel, Inc., Seoul (KR)

( * ) Notice: Subject to any disclaimer, the term of this patent is extended or adjusted under 35 U.S.C. 154(b) by 183 days.

(21) Appl. No.: 18/930,378

(22) Filed: Oct. 29, 2024

(65) Prior Publication Data

US 2025/0139779 A1 May 1, 2025

(30) Foreign Application Priority Data

Oct. 31, 2023 (KR) ........................ 10-2023-0148124
Apr. 17, 2024 (KR) ........................ 10-2024-0051729

(51) Int. Cl.
*G06T 7/00* (2017.01)
*G06T 7/73* (2017.01)
(Continued)

(52) U.S. Cl.
CPC .............. *G06T 7/0014* (2013.01); *G06T 7/73* (2017.01); *G06T 17/00* (2013.01); *A61B 6/504* (2013.01); *G06T 2207/20221* (2013.01); *G06T 2207/30096* (2013.01); *G06T 2207/30104* (2013.01); *G06T 2210/41* (2013.01); *G06T 2219/2004* (2013.01)

(58) Field of Classification Search
CPC .......... G06T 7/0014; G06T 7/73; G06T 17/00
See application file for complete search history.

(56) References Cited

U.S. PATENT DOCUMENTS 11,474,358 B2 * 10/2022 Meitav ............... G02B 27/0093
2008/0050003 A1 * 2/2008 Periaswamy ............. G06T 5/50 382/134
(Continued)

FOREIGN PATENT DOCUMENTS

CN 111134651 B 3/2022
CN 115631303 A 1/2023

OTHER PUBLICATIONS

Mar. 25, 2025—(EP) Extended European Search Report—App 24208875.5.

*Primary Examiner* — Irfan Habib
(74) *Attorney, Agent, or Firm* — Banner & Witcoff, Ltd.

(57) ABSTRACT

A method for generating three-dimensional blood vessel profile data comprises acquiring a plurality of images including blood vessels, generating three-dimensional first blood vessel profile data by using a first image and a second image of the plurality of images, generating three-dimensional second blood vessel profile data by using the second image and a third image of the plurality of images, identifying a first coordinate value corresponding to a first point in the blood vessels in the second blood vessel profile data, identifying a second coordinate value in the second image based on the first coordinate value, identifying a third coordinate value corresponding to the first point in the first blood vessel profile data based on the second coordinate value, and acquiring three-dimensional third blood vessel profile data by merging the first blood vessel profile data and the second blood vessel profile data based on the third coordinate value.

17 Claims, 17 Drawing Sheets

(51) Int. Cl.
*G06T 17/00* (2006.01)
*A61B 6/50* (2024.01)

(56) References Cited

U.S. PATENT DOCUMENTS

| | | | | |
|---|---|---|---|---|
| 2010/0021025 | A1* | 1/2010 | Hof | G06T 7/0012 382/128 |
| 2019/0156510 | A1* | 5/2019 | Mech | G06T 7/73 |
| 2019/0231220 | A1* | 8/2019 | Refai | A61B 1/00 |
| 2022/0020144 | A1* | 1/2022 | Kang | G06T 7/0012 |
| 2022/0028077 | A1* | 1/2022 | Seo | A61B 5/00 |
| 2022/0036646 | A1* | 2/2022 | Song | A61B 6/022 |
| 2025/0182270 | A1* | 6/2025 | Garcia-Garcia | G06V 10/82 |
| 2025/0209643 | A1* | 6/2025 | Lyu | G06T 7/12 |
| 2025/0227280 | A1* | 7/2025 | Liu | G06V 10/82 |

* cited by examiner

METHOD AND ELECTRONIC DEVICE FOR GENERATING 3-DIMENSIONAL BLOOD VESSEL PROFILE DATA

CROSS-REFERENCE TO RELATED APPLICATIONS

This application claims priority to Korean Patent Application No. 10-2023-0148124, filed in the Korean Intellectual Property Office on Oct. 31, 2023, and Korean Patent Application No. 10-2024-0051729, filed in the Korean Intellectual Property Office on Apr. 17, 2024, the entire contents of which are hereby incorporated by reference.

BACKGROUND

Technical Field

The present disclosure relates to a method and an electronic device for generating three-dimensional (3D) blood vessel profile data.

Description of Related Art

In the medical field, it is possible to diagnose a lesion of a subject (e.g., a patient) being examined by analyzing medical images acquired with X-rays, computed tomography (CT), angiography, etc. For example, lesions in blood vessels can be diagnosed by analyzing angiographic images. However, lesions such as myocardial ischemia caused by the coronary artery stenosis may be difficult to diagnose accurately by using only two-dimensional angiographic images. For example, there are situations where coronary artery stenosis appearing severe in imaging may not actually affect blood flow or cause myocardial ischemia, and it is thus difficult to make accurate determination of myocardial ischemia based solely on the degree of coronary artery stenosis analyzed from the two-dimensional angiographic images.

Meanwhile, blood flow characteristic values such as Fractional Flow Reserve (FFR) can be used for diagnosis in order to quickly and accurately diagnose blood vessels lesions such as coronary artery stenosis. In addition, 3D blood vessel profile data may be used to predict blood flow characteristic values. Accordingly, development of a technology is required, which can generate 3D blood vessel profile data using a plurality of 2D images so as to quickly and accurately analyze and diagnose blood vessels lesions.

SUMMARY

In order to solve one or more problems (e.g., the problems described above and/or other problems not explicitly described herein), the present disclosure provides a method and an electronic device for generating three-dimensional (3D) blood vessel profile data.

According to an aspect of the present disclosure, a method for generating three-dimensional blood vessel profile data may be performed by at least one processor and may comprise acquiring a plurality of images including blood vessels, generating three-dimensional first blood vessel profile data by using a first image and a second image of the plurality of images, generating three-dimensional second blood vessel profile data by using the second image and a third image of the plurality of images, identifying a first coordinate value corresponding to a first point in the blood vessels in the second blood vessel profile data, identifying a second coordinate value in the second image based on the first coordinate value, identifying a third coordinate value corresponding to the first point in the blood vessels in the first blood vessel profile data based on the second coordinate value, and acquiring three-dimensional third blood vessel profile data by merging at least the first blood vessel profile data and the second blood vessel profile data at least based on the third coordinate value.

According to an aspect of the present disclosure, the plurality of images may include a plurality of angiographic images acquired at different viewing angles.

According to an aspect of the present disclosure, the first point in the blood vessels may include a boundary point at which a value indicating a degree of identifying a specific region in the blood vessels in the third image is less than a value specified between proximal and distal portions of the blood vessels.

According to an aspect of the present disclosure, the method may further comprise predicting a blood flow characteristic value of the blood vessels by using the third blood vessel profile data, wherein, from a proximal portion of the blood vessels to the first point in the blood vessels, the blood flow characteristic value may correspond to a first blood flow characteristic value predicted by using the second blood vessel profile data, and from the first point in the blood vessels to a distal portion of the blood vessels, the blood flow characteristic value may correspond to a second blood flow characteristic value predicted by using the first blood vessel profile data with the first blood flow characteristic value corresponding to the first point in the blood vessels as an initial value.

According to an aspect of the present disclosure, the method may further comprise generating three-dimensional fourth blood vessel profile data by using the first image and a fourth image of the plurality of images, identifying a third-dimensional fourth coordinate value corresponding to a second point in the blood vessels in the third blood vessel profile data, identifying a two-dimensional fifth coordinate value in the first image based on the fourth coordinate value, identifying a three-dimensional sixth coordinate value corresponding to the second point in the blood vessels in the fourth blood vessel profile data based on the fifth coordinate value, and acquiring three-dimensional fifth blood vessel profile data by merging at least the third blood vessel profile data and the fourth blood vessel profile data at least based on the sixth coordinate value.

According to an aspect of the present disclosure, the method may further comprise generating three-dimensional sixth blood vessel profile data by using the first image and a fifth image of the plurality of images, identifying a three-dimensional seventh coordinate value corresponding to a third point in the blood vessels in the sixth blood vessel profile data, identifying a two-dimensional eighth coordinate value in the first image based on the seventh coordinate value, and identifying a three-dimensional ninth coordinate value corresponding to the third point in the blood vessels in the fourth blood vessel profile data based on the eighth coordinate value, wherein the acquiring the fifth blood vessel profile data may include acquiring the fifth blood vessel profile data by merging at least the third blood vessel profile data, the fourth blood vessel profile data, and the sixth blood vessel profile data at least based on the sixth coordinate value and the ninth coordinate value.

According to an aspect of the present disclosure, the method may further comprise generating three-dimensional fourth blood vessel profile data by using the second image and a fourth image of the plurality of images, identifying a three-dimensional fourth coordinate value corresponding to a second point in the blood vessels in the fourth blood vessel profile data, identifying a two-dimensional fifth coordinate value in the second image based on the fourth coordinate value, and identifying a three-dimensional sixth coordinate value corresponding to the second point in the blood vessels in the first blood vessel profile data based on the fifth coordinate value, wherein the acquiring the third blood vessel profile data may include acquiring the third blood vessel profile data by merging at least the first blood vessel profile data, the second blood vessel profile data, and the fourth blood vessel profile data at least based on the third coordinate value and the sixth coordinate value.

According to an aspect of the present disclosure, the method may further comprise generating three-dimensional fourth blood vessel profile data by using the first image and a fourth image of the plurality of images, identifying a three-dimensional fourth coordinate value corresponding to a second point in the blood vessels in the fourth blood vessel profile data, identifying a two-dimensional fifth coordinate value in the first image based on the fourth coordinate value, identifying a three-dimensional sixth coordinate value corresponding to the second point in the blood vessels in the first blood vessel profile data based on the fifth coordinate value, wherein the acquiring the third blood vessel profile data may include acquiring the third blood vessel profile data by merging at least the first blood vessel profile data, the second blood vessel profile data, and the fourth blood vessel profile data at least based on the third coordinate value and the sixth coordinate value.

There is provided a non-transitory computer-readable recording medium storing instructions for executing the method for generating three-dimensional blood vessel profile data on a computer.

According to an aspect of the present disclosure, an electronic device may comprise a memory and one or more processors connected to the memory and configured to execute one or more computer-readable programs included in the memory, wherein the one or more programs may include instructions for acquiring a plurality of images including blood vessels, generating three-dimensional first blood vessel profile data by using a first image and a second image of the plurality of images, generating three-dimensional second blood vessel profile data by using the second image and a third image of the plurality of images, identifying a first coordinate value corresponding to a first point in the blood vessels in the second blood vessel profile data, identifying a second coordinate value in the second image based on the first coordinate value, identifying a third coordinate value corresponding to the first point in the blood vessels in the first blood vessel profile data based on the second coordinate value, and acquiring three-dimensional third blood vessel profile data by merging at least the first blood vessel profile data and the second blood vessel profile data at least based on the third coordinate value.

According to an aspect of the present disclosure, the plurality of images may include a plurality of angiographic images acquired at different viewing angles.

According to an aspect of the present disclosure, the first point in the blood vessels may include a boundary point at which a value indicating a degree of identifying a specific region in the blood vessels in the third image is less than a value specified between proximal and distal portions of the blood vessels.

According to an aspect of the present disclosure, the one or more programs may further include instructions for predicting a blood flow characteristic value of the blood vessels by using the third blood vessel profile data, and the blood flow characteristic value may correspond to a first blood flow characteristic value predicted by using the second blood vessel profile data from a proximal portion of the blood vessels to the first point in the blood vessels, and the blood flow characteristic value may correspond to a second blood flow characteristic value predicted by using the first blood vessel profile data with the first blood flow characteristic value corresponding to the first point in the blood vessels as an initial value from the first point in the blood vessels to a distal portion of the blood vessels.

According to an aspect of the present disclosure, the one or more programs may further include instructions for generating three-dimensional fourth blood vessel profile data by using the first image and a fourth image of the plurality of images, identifying a third-dimensional fourth coordinate value corresponding to a second point in the blood vessels in the third blood vessel profile data, identifying a two-dimensional fifth coordinate value in the first image based on the fourth coordinate value, identifying a three-dimensional sixth coordinate value corresponding to the second point in the blood vessels in the fourth blood vessel profile data based on the fifth coordinate value, and acquiring three-dimensional fifth blood vessel profile data by merging at least the third blood vessel profile data and the fourth blood vessel profile data at least based on the sixth coordinate value.

According to an aspect of the present disclosure, the one or more programs may further include instructions for generating three-dimensional sixth blood vessel profile data by using the first image and a fifth image of the plurality of images, identifying a three-dimensional seventh coordinate value corresponding to a third point in the blood vessels in the sixth blood vessel profile data, identifying a two-dimensional eighth coordinate value in the first image based on the seventh coordinate value, and identifying a three-dimensional ninth coordinate value corresponding to the third point in the blood vessels in the fourth blood vessel profile data based on the eighth coordinate value, and the acquiring the fifth blood vessel profile data may include acquiring the fifth blood vessel profile data by merging at least the third blood vessel profile data, the fourth blood vessel profile data, and the sixth blood vessel profile data at least based on the sixth coordinate value and the ninth coordinate value.

According to an aspect of the present disclosure, the one or more programs may further include instructions for generating three-dimensional fourth blood vessel profile data by using the second image and a fourth image of the plurality of images, identifying a three-dimensional fourth coordinate value corresponding to a second point in the blood vessels in the fourth blood vessel profile data, identifying a two-dimensional fifth coordinate value in the second image based on the fourth coordinate value, and identifying a three-dimensional sixth coordinate value corresponding to the second point in the blood vessels in the first blood vessel profile data based on the fifth coordinate value, and the acquiring the third blood vessel profile data may include acquiring the third blood vessel profile data by merging at least the first blood vessel profile data, the second blood vessel profile data, and the fourth blood vessel profile data at least based on the third coordinate value and the sixth coordinate value.

According to an aspect of the present disclosure, the one or more programs may further include instructions for generating three-dimensional fourth blood vessel profile data by using the first image and a fourth image of the plurality of images, identifying a three-dimensional fourth coordinate value corresponding to a second point in the blood vessels in the fourth blood vessel profile data, identifying a two-dimensional fifth coordinate value in the first image based on the fourth coordinate value, identifying a three-dimensional sixth coordinate value corresponding to the second point in the blood vessels in the first blood vessel profile data based on the fifth coordinate value, and the acquiring the third blood vessel profile data may include acquiring the third blood vessel profile data by merging at least the first blood vessel profile data, the second blood vessel profile data, and the fourth blood vessel profile data at least based on the third coordinate value and the sixth coordinate value.

According to some aspects of the present disclosure, by generating the 3D blood vessel profile data using a plurality of two-dimensional images, it is possible to facilitate prediction of blood flow characteristic values, and to quickly and accurately analyze and diagnose blood vessels lesions through the predicted blood flow characteristic values.

The effects of the present disclosure are not limited to the effects described above, and other effects not described herein can be clearly understood by those of ordinary skill in the art (referred to as "ordinary technician") from the description of the claims.

BRIEF DESCRIPTION OF THE DRAWINGS

The above and other objects, features and advantages of the present disclosure will be described with reference to the accompanying drawings described below, where similar reference numerals indicate similar elements, but not limited thereto, in which.

DETAILED DESCRIPTION

Figure 1:
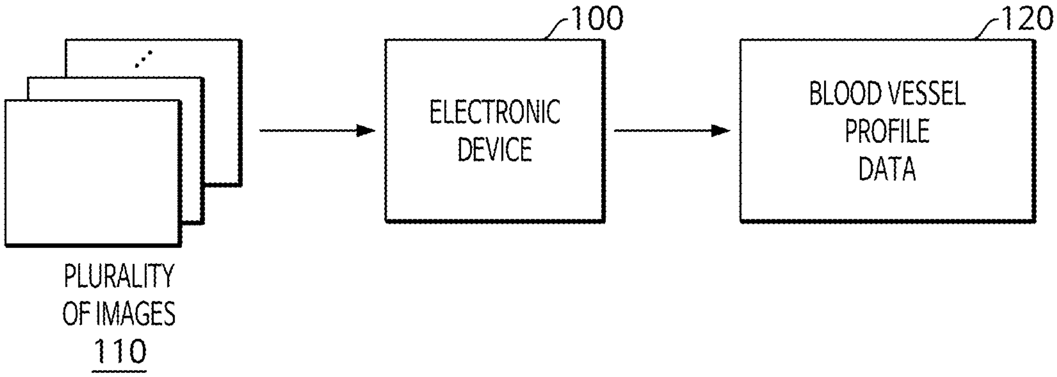
FIG. 1 is a diagram illustrating an example of an electronic device for generating three-dimensional (3D) blood vessel profile data according to an aspect of the present disclosure.

Hereinafter, example details for the practice of the present disclosure will be described in detail with reference to the accompanying drawings. However, in the following description, detailed descriptions of well-known functions or configurations will be omitted if it may make the subject matter of the present disclosure rather unclear.

In the accompanying drawings, the same or corresponding components are assigned the same reference numerals. In addition, in the following description of various examples, duplicate descriptions of the same or corresponding components may be omitted. However, even if descriptions of components are omitted, it is not intended that such components are not included in any example.

Advantages and features of the disclosed examples and methods of accomplishing the same will be apparent by referring to examples described below in connection with the accompanying drawings. However, the present disclosure is not limited to the examples disclosed below, and may be implemented in various forms different from each other, and the examples are merely provided to make the present disclosure complete, and to fully disclose the scope of the disclosure to those skilled in the art to which the present disclosure pertains.

The terms used herein will be briefly described prior to describing the disclosed example(s) in detail. The terms used herein have been selected as general terms which are widely used at present in consideration of the functions of the present disclosure, and this may be altered according to the intent of an operator skilled in the art, related practice, or introduction of new technology. In addition, in specific cases, certain terms may be arbitrarily selected by the applicant, and the meaning of the terms will be described in detail in a corresponding description of the example(s). Accordingly, the terms used in this disclosure should be defined based on the meaning of the term and the overall content of the present disclosure, rather than simply the name of the term.

As used herein, the singular forms "a," "an," and "the" are intended to include the plural forms as well, unless the context clearly indicates the singular forms. Further, the plural forms are intended to include the singular forms as well, unless the context clearly indicates the plural forms.

Further, throughout the description, when a portion is stated as "comprising (including)" a component, it is intended as meaning that the portion may additionally comprise (or include or have) another component, rather than excluding the same, unless specified to the contrary.

Further, the term "module" or "unit" used herein refers to a software or hardware component, and "module" or "unit" performs certain roles. However, the meaning of the "module" or "unit" is not limited to software or hardware. The "module" or "unit" may be configured to be in an addressable storage medium or configured to play one or more processors. Accordingly, as an example, the "module" or "unit" may include components such as software components, object-oriented software components, class components, and task components, and at least one of processes, functions, attributes, procedures, subroutines, program code segments, drivers, firmware, micro-codes, circuits, data, database, data structures, tables, arrays, and variables. Furthermore, functions provided in the components and the "modules" or "units" may be combined into a smaller number of components and "modules" or "units", or further divided into additional components and "modules" or "units."

A "module" or "unit" may be implemented as a processor and a memory, or may be implemented as a circuit (circuitry). Terms such as circuit and circuitry may refer to circuits in hardware, but may also refer to circuits in software. The "processor" should be interpreted broadly to encompass a general-purpose processor, a central processing unit (CPU), a microprocessor, a digital signal processor (DSP), a neural processing unit (NPU), a controller, a microcontroller, a state machine, etc. Under some circumstances, the "processor" may refer to an application-specific integrated circuit (ASIC), a programmable logic device (PLD), a field-programmable gate array (FPGA), etc. The "processor" may refer to a combination for processing devices, e.g., a combination of a DSP and a microprocessor, a combination of a plurality of microprocessors, a combination of one or more microprocessors in conjunction with a DSP core, or any other combination of such configurations. In addition, the "memory" should be interpreted broadly to encompass any electronic component that is capable of storing electronic information. The "memory" may refer to various types of processor-readable media such as random access memory (RAM), read-only memory (ROM), non-volatile random access memory (NVRAM), programmable read-only memory (PROM), erasable programmable read-only memory (EPROM), electrically erasable PROM (EEPROM), flash memory, magnetic or optical data storage, registers, etc. The memory is said to be in electronic communication with a processor if the processor can read information from and/or write information to the memory. The memory integrated with the processor is in electronic communication with the processor.

In addition, terms such as first, second, A, B, (a), (b), etc. used in the following examples are only used to distinguish certain components from other components, and the nature, sequence, order, etc. of the components are not limited by the terms.

In addition, in the following examples, if a certain component is stated as being "connected," "combined" or "coupled" to another component, it is to be understood that there may be yet another intervening component "connected," "combined" or "coupled" between the two components, although the two components may also be directly connected or coupled to each other.

In addition, as used in the following examples, "comprise" and/or "comprising" does not foreclose the presence or addition of one or more other elements, steps, operations, and/or devices in addition to the recited elements, steps, operations, or devices.

Hereinafter, various examples of the present disclosure will be described in detail with reference to the accompanying drawings.

FIG. 1 is a diagram illustrating an example of an electronic device for generating three-dimensional (3D) blood vessel profile data according to an aspect of the present disclosure. Referring to FIG. 1, an electronic device 100 may generate 3D blood vessel profile data 120 based on a plurality of images 110 including blood vessels. The plurality of images 110 including blood vessels may refer to medical images of all types of modalities, including X-ray images, ultrasound images, chest radiographic images, computed tomography (CT) images, positron emission tomography (PET) images, magnetic resonance imaging (MRI) images, sonography (ultrasound (US)) images, functional MRI (fMRI) images, digital pathology Whole Slide Image (WSI), digital breast tomosynsis (DBT) images, etc. For example, each of the plurality of images 110 including blood vessels may include a medical image obtained by capturing images of blood vessels of a target patient who is administered a contrast agent. In addition, the blood vessel profile data 120 may include not only data representing the construction of the blood vessels, but also data about the construction of the blood vessels itself (e.g., a 3D reconstructed blood vessel model) or data corresponding to the construction of the blood vessels (e.g., FFR data corresponding to a 3D blood vessel model).

Although FIG. 1 does not illustrate a storage system capable of communication with the electronic device 100, the electronic device 100 may be connected to, or configured to communicate with one or more storage systems. The storage system connected to or configured to communicate with the electronic device 100 may include a device or a cloud system that stores and manages various data associated with the operation of generating the 3D blood vessel profile data 120 based on the plurality of images 110. For efficient data management, the storage system may store and manage various types of data using a database. The various types of data may include any data associated with the generation of the blood vessel profile data 120. For example, the various data may include, but are not limited to, a machine learning model, training data, the plurality of images 110, etc. associated with the generation of the blood vessel profile data 120.

The electronic device 100 may acquire the plurality of images 110 including blood vessels. The electronic device 100 may generate a plurality of 3D blood vessel profile data using at least two or more of the plurality of images 110. For example, the electronic device 100 may generate 3D first blood vessel profile data using a first image and a second image of the plurality of images 110, and may generate 3D second blood vessel profile data using the second image and a third image of the plurality of images 110. In this case, there may be an image, among the plurality of images 110, that is commonly used when generating the plurality of blood vessel profile data, and such an image may be referred to as a bridge image in the following description. For example, if the first and second images are used for generating the first blood vessel profile data and the second and third images are used for generating the second blood vessel profile data, the second image may be the bridge image. One or more bridge images may be used depending on a method for generating 3D blood vessel profile data.

As described above, if the plurality of blood vessel profile data (e.g., first blood vessel profile data and second blood vessel profile data) are generated by using at least one bridge image, the electronic device 100 may acquire the 3D blood vessel profile data by merging the plurality of blood vessel profile data. For example, the electronic device 100 may acquire third blood vessel profile data by merging the first blood vessel profile data and the second blood vessel profile data. In this case, the electronic device 100 may use the bridge image to merge the plurality of blood vessel profile data. For example, the electronic device 100 may identify a first coordinate value corresponding to a specific point in the blood vessels from any one of the plurality of blood vessel profile data. The specific point in the blood vessels may include a boundary point where the identification of the blood vessels can be determined. For example, the specific point in blood vessels may include a boundary point at which a value indicating a degree of identifying a specific region in the blood vessels in the image is less than a specified value between proximal and distal portions of the blood vessels. The electronic device 100 may identify the second coordinate value in the bridge image based on the identified first coordinate value. For example, the electronic device 100 may identify a two-dimensional second coordinate value corresponding to the 3D first coordinate value. The electronic device 100 may identify a third coordinate value corresponding to the specific point in the blood vessels from another blood vessel profile data of the plurality of blood vessel profile data based on the identified second coordinate value. For example, the electronic device 100 may identify the third coordinate value in another blood vessel profile data corresponding to the first coordinate value in any one blood vessel profile data, using the second coordinate value in the commonly used bridge image. The electronic device 100 may merge the plurality of blood vessel profile data based on the identified third coordinate value. For example, the electronic device 100 may acquire the 3D third blood vessel profile data by merging the first blood vessel profile data and the second blood vessel profile data which are generated by using the bridge image in common.

Figure 2:
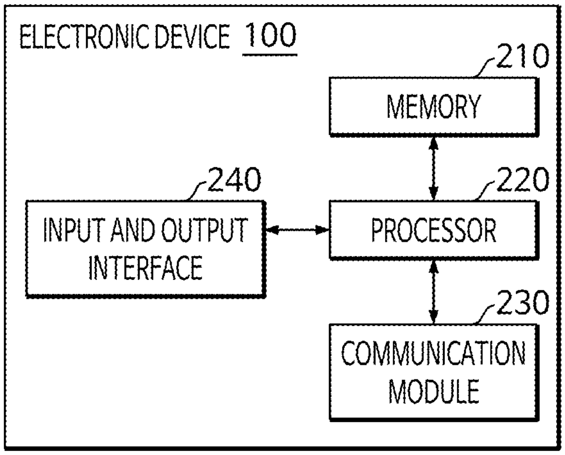
FIG. 2 is a diagram provided to explain a configuration of the electronic device according to an aspect of the present disclosure.

FIG. 2 is a diagram provided to explain a configuration of the electronic device according to an aspect of the present disclosure. Referring to FIG. 2, the electronic device 100 may include a memory 210, a processor 220, a communication module 230, and an input and output interface 240. However, the configuration of the electronic device 100 is not limited to the above. According to various aspects, the electronic device 100 may omit at least one of the components described above, and may further include at least one more additional component. For example, the electronic device 100 may further include a display. In this case, the electronic device 100 may display, on the display, at least one of a medical image obtained by capturing images of blood vessels (e.g., the plurality of images 110 in FIG. 1) or the blood vessel profile data 120.

The memory 210 may store various data used by at least one (e.g., the processor 220) of the other components of the electronic device 100. For example, the data may include input data or output data for software (e.g., a program) and commands related to the same.

The memory 210 may include any non-transitory computer-readable recording medium. The memory 210 may include a permanent mass storage device such as disk drive, solid state drive (SSD), flash memory, etc. As another example, a non-destructive mass storage device such as ROM, SSD, flash memory, disk drive, etc. may be included in the electronic device 100 as a separate permanent storage device that is separate from the memory 210. In addition, the memory 210 may store an operating system and at least one program code (e.g., instructions installed and driven in the electronic device 100 for generation of the blood vessel profile data). In FIG. 2, the memory 210 is illustrated as a single memory, but this is only for convenience of description, and the memory 210 may include a plurality of memories and/or buffer memories.

Software components may be loaded from a computer-readable recording medium separate from the memory 210. Such a separate computer-readable recording medium may include a recording medium directly connectable to the electronic device 100, and may include, for example, a computer-readable recording medium such as a floppy drive, a disk, a tape, a DVD/CD-ROM drive, a memory card, etc. In another example, the software components may be loaded into the memory 210 through the communication module 230 rather than the computer-readable recording medium. For example, at least one program may be loaded into the memory 210 based on a computer program (e.g., a program, etc. for transmitting data such as medical images obtained by capturing images of blood vessels) installed by the files provided by the developers, or by a file distribution system that distributes an installation file of an application through the communication module 230.

The processor 220 may execute software (or program) to control at least one of the other components (e.g., hardware or software component) of the electronic device 100 connected to the processor 220, and may perform various data processing or operations. The processor 220 may, as at least part of the data processing or operation, load a command or data received from other components (e.g., the communication module 230) into a volatile memory, process the command or data stored in the volatile memory, and store the result data in a non-volatile memory.

The processor 220 may be configured to process the commands of the computer program by performing basic arithmetic, logic, and input and output operations. The commands may be provided to the electronic device 100 or another external system by the memory 210 or the communication module 230. For example, the processor 220 may generate 3D blood vessel profile data. The processor 220 may store the generated 3D blood vessel profile data in the memory 210, display the same on the display of the electronic device 100, or transmit the same to an external electronic device through the communication module 230. Alternatively, the processor 220 may perform an additional analysis operation such as predicting blood flow characteristic value, etc., by using the 3D blood vessel profile data. In FIG. 2, the processor 220 is illustrated as a single processor, but this is only for convenience of description, and the processor 220 may include a plurality of processors.

The communication module 230 may support establishment of a direct (e.g., wired) communication channel or wireless communication channel between the electronic device 100 and an external electronic device and performance of communication through the established communication channel. For example, the communication module 230 may provide a configuration or function for the electronic device 100 and the external electronic device (e.g., user terminal or cloud server) to communicate with each other through a network. For example, control signals, commands, data, etc. provided under the control of the processor 220 of the electronic device 100 may be transmitted to an external electronic device through the communication module 230 and the network and through the communication module of the external electronic device. For example, the electronic device 100 may receive a medical image obtained by capturing images of blood vessels of a subject from the external electronic device through the communication module 230.

The input and output interface 240 may be a means for interfacing with a device (not illustrated) for input or output, which may be connected to or included in the electronic device 100. For example, the input and output interface 240 may include at least one of a PCI express interface and an Ethernet interface. In FIG. 2, the input and output interface 240 is illustrated as a component configured separately from the processor 220, but aspects are not limited thereto, and the input and output interface 240 may be configured to be included in the processor 220.

The processor 220 may perform a function related to the generation of 3D blood vessel profile data. The processor 220 may execute at least one computer-readable program included in the memory 210 to perform a function related to the generation of 3D blood vessel profile data. The at least one program may include instructions for acquiring a plurality of images including blood vessels, generating 3D first blood vessel profile data by using a first and second images of the plurality of images, generating 3D second blood vessel profile data by using the second and third images of the plurality of images, identifying a first coordinate value corresponding to a first point in the blood vessels in the second blood vessel profile data, identifying, based on the first coordinate value, a second coordinate value in the second image, identifying, based on the second coordinate value, a third coordinate value corresponding to the first point in the blood vessels in the first blood vessel profile data, and acquiring 3D third blood vessel profile data by merging at least the first blood vessel profile data and the second blood vessel profile data at least based on the third coordinate value. In the following description, for convenience of explanation, when it is described that the processor 220 executes at least one program to perform a function related to the generation of 3D blood vessel profile data, it may describe the processor 220 performing a function related to the generation of 3D blood vessel profile data. For example, when it is described that the at least one program includes instructions related to the generation of 3D blood vessel profile data, it may correspond to the processor 220 performing a function related to the generation of 3D blood vessel profile data.

Figure 3:
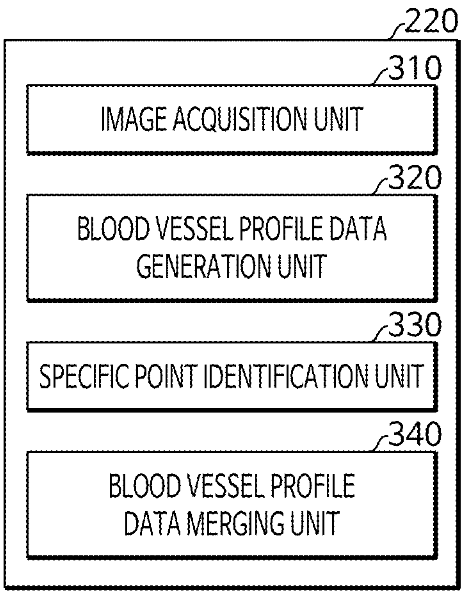
FIG. 3 is a diagram provided to explain a configuration of the processor of the electronic device according to an aspect of the present disclosure.

FIG. 3 is a diagram provided to explain a configuration of the processor of the electronic device according to an aspect of the present disclosure. Referring to FIG. 3, the processor 220 may generate 3D blood vessel profile data (e.g., the blood vessel profile data 120 of FIG. 1) based on a plurality of images including blood vessels (e.g., the plurality of images 110 of FIG. 1). To this end, the processor 220 may include an image acquisition unit 310, a blood vessel profile data generation unit 320, a specific point identification unit 330, and a blood vessel profile data merging unit 340. However, the types of components included in the processor 220 are classified according to functions related to the generation of 3D blood vessel profile data, and the types and numbers thereof are not limited thereto. In addition, at least one of the components included in a processor 200 may be implemented in the form of instructions stored in the memory (e.g., the memory 210 of FIG. 2).

The image acquisition unit 310 may acquire a plurality of images (e.g., the plurality of images 110 of FIG. 1) including blood vessels. The processor 220 may acquire a medical image obtained by capturing images of blood vessels of the target patient administered a contrast agent. For example, the plurality of images may include a plurality of angiographic images acquired at different viewing angles. This medical images may be received from a storage system (e.g., hospital system, electronic medical records, prescription delivery system, medical imaging system, inspection information system, local/cloud storage system, etc.) connected to or capable of communicating with the electronic device, an internal memory and/or a user terminal, etc. The image acquisition unit 310 may provide at least one of the acquired images to the blood vessel profile data generation unit 320, the specific point identification unit 330, and/or the blood vessel profile data merging unit 340.

The blood vessel profile data generation unit 320 may generate a plurality of 3D blood vessel profile data by using at least two images of the plurality of images acquired through the image acquisition unit 310. For example, the blood vessel profile data generation unit 320 may generate the 3D first blood vessel profile data by using a first image and a second image of the plurality of images. Additionally or alternatively, the blood vessel profile data generation unit 320 may generate the 3D second blood vessel profile data by using the second image and a third image of the plurality of images.

The specific point identification unit 330 may identify a specific point in the blood vessels included in the image. The specific point in the blood vessels may include a boundary point where the identification of the blood vessels can be determined. For example, the specific point in blood vessels may include a boundary point at which a value indicating a degree of identifying a specific region in the blood vessels in the image is less than a specified value between proximal and distal portions of the blood vessels. According to another aspect, the specific point in the blood vessels may refer to a common point in at least two images such as a branch, but aspects are not limited thereto.

The blood vessel profile data merging unit 340 may acquire 3D blood vessel profile data by merging the plurality of blood vessel profile data. For example, the blood vessel profile data merging unit 340 may acquire the third blood vessel profile data by merging the first blood vessel profile data and the second blood vessel profile data. The blood vessel profile data merging unit 340 may use the bridge image to merge the plurality of blood vessel profile data. The bridge image may refer to an image that is commonly used for generating the plurality of blood vessel profile data used for merging. For example, if the first and second images are used for generating the first blood vessel profile data and the second and third images are used for generating the second blood vessel profile data, the second image may be the bridge image. One or more bridge images may be used depending on a method for generating 3D blood vessel profile data.

According to another aspect, the blood vessel profile data merging unit 340 may generate 3D blood vessel profile data by merging the first blood vessel profile data and the second blood vessel profile data using a common point in the at least one image used for generating the first blood vessel profile data and the at least one image used for generating the second blood vessel profile data. A method of generating new 3D blood vessel profile data by merging the plurality of 3D blood vessel profile data using this common point will be described below with reference to FIGS. 15 to 17.

In the blood vessel profile data merging process, the blood vessel profile data merging unit 340 may identify a first coordinate value corresponding to the specific point in the blood vessels from any one blood vessel profile data of the plurality of blood vessel profile data. The specific point in the blood vessels may be identified through the specific point identification unit 330. The blood vessel profile data merging unit 340 may identify the second coordinate value in the bridge image based on the identified first coordinate value. For example, the blood vessel profile data merging unit 340 may identify a 2D second coordinate value corresponding to the 3D first coordinate value. The blood vessel profile data merging unit 340 may identify a third coordinate value corresponding to the specific point in the blood vessels from another blood vessel profile data of the plurality of blood vessel profile data based on the identified second coordinate value. For example, the blood vessel profile data merging unit 340 may identify the third coordinate value in another blood vessel profile data corresponding to the first coordinate value in any one blood vessel profile data by using the second coordinate value in the commonly used bridge image. The blood vessel profile data merging unit 340 may merge the plurality of blood vessel profile data based on the identified third coordinate value.

The processor 220 may predict a blood flow characteristic value of the blood vessels by using the merged blood vessel profile data (e.g., the third blood vessel profile data). For example, the blood flow characteristic value may include Fractional Flow Reserve (FFR). If there is a lesion in the blood vessels, the perfusion pressure decreases, resulting in a pressure difference between the distal and proximal portions of the lesion site, and the FFR may represent a value of assessing this difference. The processor 220 may predict the blood flow characteristic value of the blood vessels through a machine learning model using the blood vessel profile data as an input. The machine learning model may include any model used to infer an answer to a given input. The machine learning model may include an artificial neural network model including an input layer, a plurality of hidden layers, and an output layer. In an example, each layer may include one or more nodes. In addition, the machine learning model may include weights associated with a plurality of nodes included in the machine learning model. In an example, the weights may include any parameter associated with the machine learning model. In some aspects, the machine learning model may be a model trained with various training methods. For example, according to various aspects, various learning methods such as supervised learning, semi-supervised learning, unsupervised learning (or self-learning), reinforcement learning, etc. may be used. Throughout the description, the machine learning model may refer to an artificial neural network model, and the artificial neural network model may refer to the machine learning model.

From the proximal portion of the blood vessels to the specific point in the blood vessels, the blood flow characteristic value of the blood vessels predicted by using the blood vessel profile data may correspond to the first blood flow characteristic value predicted by using the second blood vessel profile data. In addition, from the specific point in the blood vessels to the distal portion of the blood vessels, the blood flow characteristic value of the blood vessels may correspond to the second blood flow characteristic value predicted by using the first blood vessel profile data with the first blood flow characteristic value corresponding to the specific point in the blood vessels as an initial value.

For the method for acquiring the blood vessel profile data using a plurality of images exceeding three images, various methods may be used depending on which image of the plurality of images is used as the bridge image. Such a method may include, for example, a chain coupling method, a one bridge coupling method, a side coupling method, or a combination thereof. The method for acquiring blood vessel profile data using the plurality of images exceeding three images will be described in detail with reference to FIGS. 7 to 13.

Figure 4:
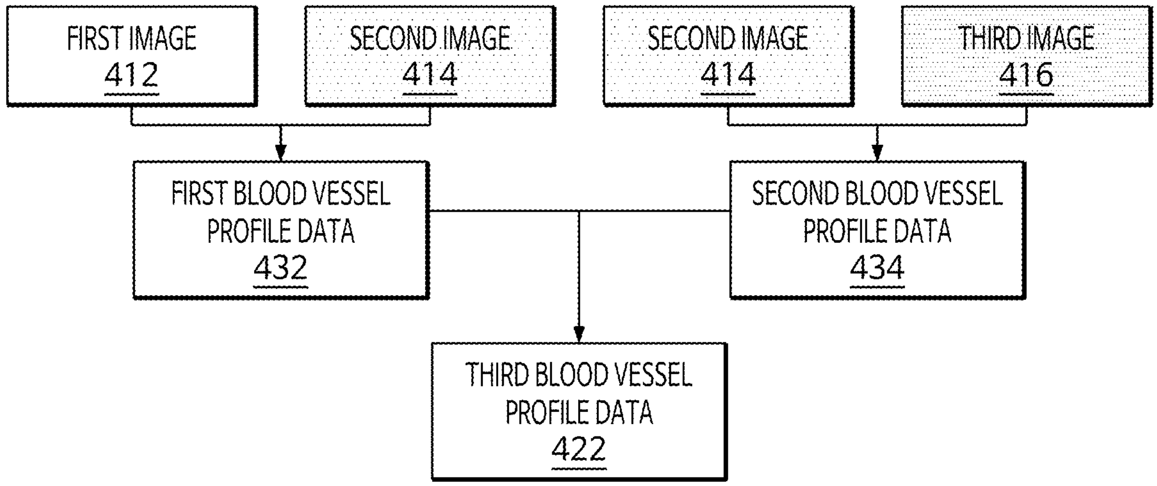
FIG. 4 is a diagram provided to explain a first method for generating 3D blood vessel profile data according to an aspect of the present disclosure.
Figure 5:
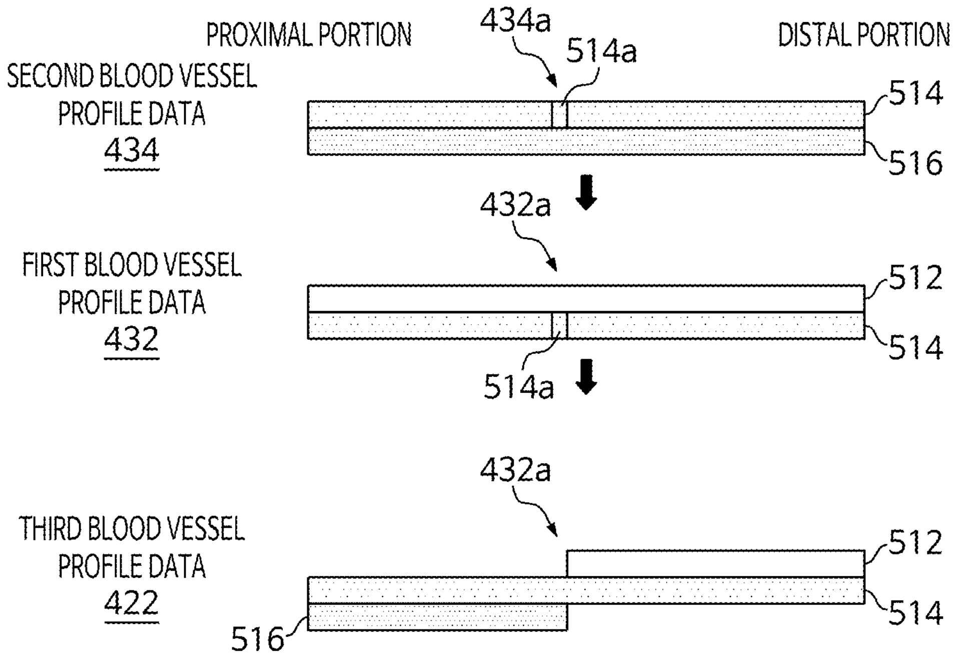
FIG. 5 is a diagram schematically illustrating image information included in the blood vessel profile data by the first method for generating the 3D blood vessel profile data according to an aspect of the present disclosure.
Figure 6:
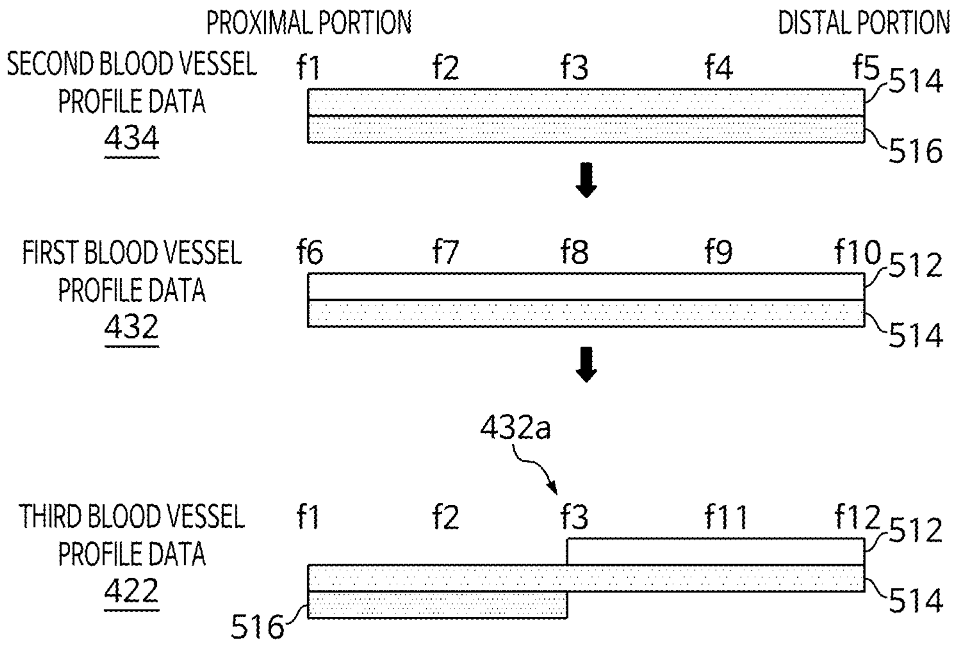
FIG. 6 is a diagram provided to explain a method for predicting a blood flow characteristic value by the first method for generating the 3D blood vessel profile data according to an aspect of the present disclosure.

FIG. 4 is a diagram provided to explain a first method for generating 3D blood vessel profile data according to an aspect of the present disclosure, FIG. 5 is a diagram schematically illustrating image information included in the blood vessel profile data by the first method for generating the 3D blood vessel profile data according to an aspect of the present disclosure, and FIG. 6 is a diagram provided to explain a method for predicting a blood flow characteristic value by the first method for generating the 3D blood vessel profile data according to an aspect of the present disclosure. Referring to FIGS. 4 to 6, the processor (e.g., the processor 220 of FIGS. 2 and 3) of the electronic device (e.g., the electronic device 100 of FIGS. 1 and 2) may generate 3D blood vessel profile data 432, 434, and 422 based on a plurality of images 412, 414, and 416 including blood vessels. A method for acquiring the blood vessel profile data using three images will be described with reference to FIGS. 4 and 5. In FIG. 5, a plurality of image data 512, 514, and 516 used for generating the blood vessel profile data 432, 434, and 422 may correspond to the plurality of images 412, 414, and 416, and they are illustrated in the form of straight lines for convenience of explanation. For example, the first image data 512 may correspond to the first image 412, the second image data 514 may correspond to the second image 414, and the third image data 516 may correspond to the third image 416.

According to the method for acquiring the blood vessel profile data, the processor may generate the 3D first blood vessel profile data 432 by using the first image 412 and the second image 414. For example, the processor may generate the first blood vessel profile data 432 by using the first image data 512 and the second image data 514. In addition, the processor may generate the 3D second blood vessel profile data 434 by using the second image 414 and the third image 416. For example, the processor may generate the second blood vessel profile data 434 by using the second image data 514 and the third image data 516. In this case, the second image 414 may be a bridge image that is commonly used for generating the first blood vessel profile data 432 and the second blood vessel profile data 434.

If the first blood vessel profile data 432 and the second blood vessel profile data 434 are generated by using the bridge image, the processor may acquire the 3D third blood vessel profile data 422 by merging the first blood vessel profile data 432 and the second blood vessel profile data 434. In more detail, the processor may identify a first coordinate value 434*a* corresponding to a first point in the blood vessels in the second blood vessel profile data 434. For example, based on the assumption that the proximal portion of the blood vessels is the origin in the 3D coordinate system in the second blood vessel profile data 434, the processor may identify the first coordinate value 434*a* corresponding to the first point in the blood vessels. In addition, the processor may acquire a predicted blood flow characteristic value f3 at the first coordinate value 434*a* corresponding to the first point in the blood vessels. The first point in the blood vessels may include a boundary point where the identification of the blood vessels can be determined. For example, the first point in the blood vessels may include a boundary point at which a value indicating a degree of identifying a specific region in the blood vessels in the image (e.g., in the second image 414 or the third image 416) used for generating the second blood vessel profile data 434 or the second blood vessel profile data 434 is less than a value specified between the proximal and distal portions of the blood vessels.

The processor may identify a second coordinate value 514*a* in the second image 414 that is the bridge image based on the first coordinate value 434*a*. For example, the processor may identify a 2D second coordinate value 514*a* corresponding to the 3D first coordinate value 434*a*. The processor may identify the 2D second coordinate value 514*a* in the second image 414 from the 3D first coordinate value 434*a* by using a back projection method, etc.

The processor may identify a third coordinate value 432*a* corresponding to the first point in the blood vessels in the first blood vessel profile data 432 based on the second coordinate value 514*a*. For example, the processor may identify the third coordinate value 432*a* in the first blood vessel profile data 432 corresponding to the first coordinate value 434*a* in the second blood vessel profile data 434 by using the second coordinate value 514*a* in the commonly used bridge image (e.g., in the second image 414). In addition, the processor may inject (or substitute) the predicted blood flow characteristic value f3 at the first coordinate value 434*a* corresponding to the first point in the blood vessels into the third coordinate value 432*a* in the first blood vessel profile data 432.

The processor may acquire the 3D third blood vessel profile data 422 by merging at least the first blood vessel profile data 432 and the second blood vessel profile data 434 at least based on the third coordinate value 432*a*. In this way, the 3D third blood vessel profile data 422 may be acquired by merging the first blood vessel profile data 432 and the second blood vessel profile data 434 generated based on the second image 414 that is the bridge image. In this case, from the proximal portion of the blood vessels to the first point in the blood vessels, the third blood vessel profile data 422 may be acquired by using the second blood vessel profile data 434, and from the first point in the blood vessels to the distal portion of the blood vessels, the third blood vessel profile data 422 may be acquired by using the first blood vessel profile data 432. In this process, the processor may recalculate the blood flow characteristic value of the blood vessels in the third blood vessel profile data 422. For example, since the predicted blood flow characteristic value f3 at the first coordinate value 434*a* corresponding to the first point in the blood vessels is injected (or substituted) into the third coordinate value 432*a* in the first blood vessel profile data 432, the processor may recalculate the blood flow characteristic value by using the injected (or substituted) value f3 as an initial value. Accordingly, as illustrated in FIG. 6, from the proximal portion of the blood vessels to the first point in the blood vessels, the blood flow characteristic value of the blood vessels may correspond to the first blood flow characteristic values (f1->f2->f3) predicted by using the second blood vessel profile data, and from the first point in the blood vessels to the distal portion of the blood vessels, the blood flow characteristic value of the blood vessels may correspond to the second blood flow characteristic values (f3->f11->f12) predicted by using the first blood vessel profile data with the first blood flow characteristic value f3 corresponding to the first point in the blood vessels as an initial value.

Figure 7:
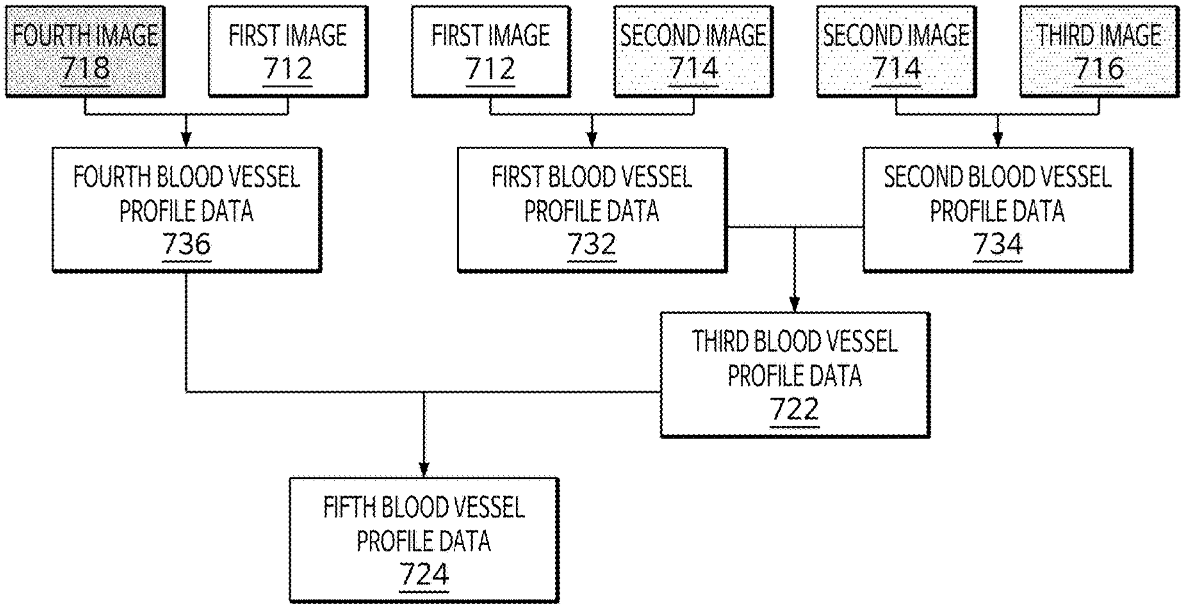
FIG. 7 is a diagram provided to explain a second method for generating 3D blood vessel profile data according to an aspect of the present disclosure.
Figure 8:
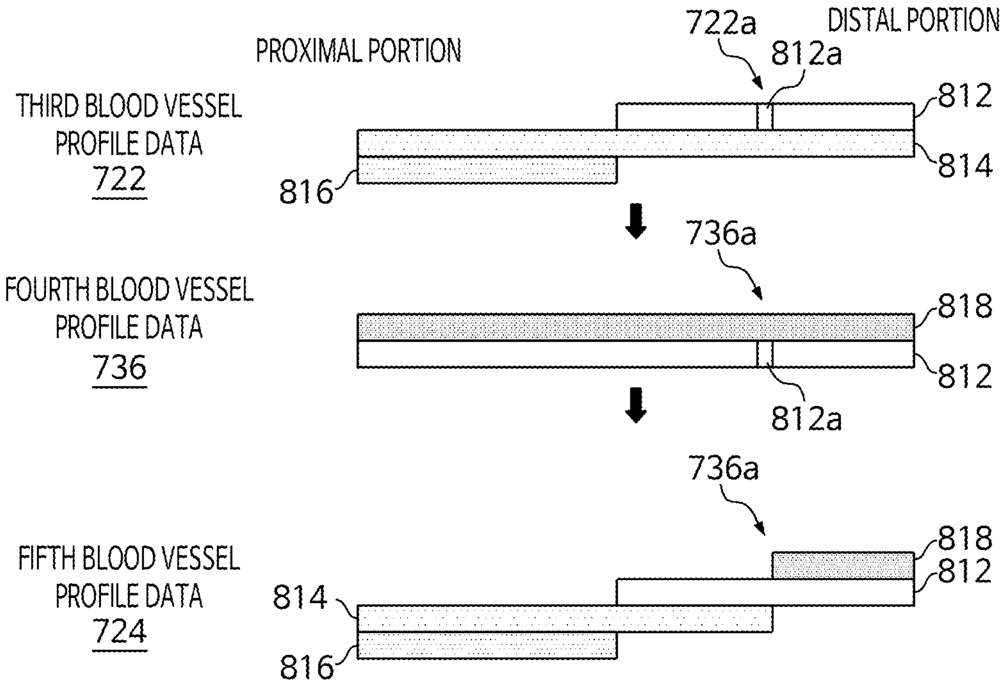
FIG. 8 is a diagram schematically illustrating image information included in the blood vessel profile data by the second method for generating the 3D blood vessel profile data according to an aspect of the present disclosure.

FIG. 7 is a diagram provided to explain a second method for generating 3D blood vessel profile data according to an aspect of the present disclosure, and FIG. 8 is a diagram schematically illustrating image information included in the blood vessel profile data by the second method for generating the 3D blood vessel profile data according to an aspect of the present disclosure. Referring to FIGS. 7 and 8, the processor (e.g., the processor 220 of FIGS. 2 and 3) of the electronic device (e.g., the electronic device 100 of FIGS. 1 and 2) may generate 3D blood vessel profile data 732, 734, 736, 722, and 724 based on a plurality of images 712, 714, 716, and 718 including blood vessels. In FIGS. 7 and 8, the chain coupling method as an example of a method for acquiring the blood vessel profile data using four images will be described. In FIG. 8, a plurality of image data 812, 814, 816, and 818 used for generating the blood vessel profile data 732, 734, 736, 722, and 724 may correspond to the plurality of images 712, 714, 716, and 718, and they are illustrated in the form of straight lines for convenience of explanation. For example, the first image data 812 may correspond to the first image 712, the second image data 814 may correspond to the second image 714, the third image data 816 may correspond to the third image 716, and the fourth image data 818 may correspond to the fourth image 718.

According to the method (chain coupling method) for acquiring the blood vessel profile data, the processor may generate the 3D first blood vessel profile data 732 by using the first image 712 and the second image 714. For example, the processor may generate the first blood vessel profile data 732 by using the first image data 812 and the second image data 814. In addition, the processor may generate the 3D second blood vessel profile data 734 by using the second image 714 and the third image 716. For example, the processor may generate the second blood vessel profile data 734 by using the second image data 814 and the third image data 816. In addition, the processor may generate the 3D fourth blood vessel profile data 736 by using the first image 712 and the fourth image 718. For example, the processor may generate the fourth blood vessel profile data 736 by using the first image data 812 and the fourth image data 818. In this case, the second image 714 may be a first bridge image that is commonly used for generating the first blood vessel profile data 732 and the second blood vessel profile data 734, and the first image 712 may be a second bridge image that is commonly used for generating the first blood vessel profile data 732 and the fourth blood vessel profile data 736.

If the first blood vessel profile data 732 and the second blood vessel profile data 734 are generated by using the first bridge image, the processor may acquire the 3D third blood vessel profile data 722 by merging the first blood vessel profile data 732 and the second blood vessel profile data 734. The process of acquiring the 3D third blood vessel profile data 722 by merging the first blood vessel profile data 732 and the second blood vessel profile data 734 may be the same as or similar to the process of acquiring the blood vessel profile data described above with reference to FIGS. 4 to 6, and thus a detailed description thereof will be omitted.

The processor may identify a 3D fourth coordinate value 722*a* corresponding to the second point in the blood vessels in the third blood vessel profile data 722. In addition, the processor may acquire a predicted blood flow characteristic value at the fourth coordinate value 722*a* corresponding to the second point in the blood vessels. The second point in the blood vessels may refer to a point different from the first point in the blood vessels described above with reference to FIGS. 4 to 6, and like the first point in the blood vessels, the second point may include a boundary point where the identification of the blood vessels can be determined. For example, the second point in the blood vessels may include a boundary point at which a value indicating a degree of identifying a specific region in the blood vessels in the image (e.g., in the first image 712, the second image 714 or the third image 716) used for generating the third blood vessel profile data 722 or the third blood vessel profile data 722 is less than a value specified between the proximal and distal portions of the blood vessels.

The processor may identify a 2D fifth coordinate value 812*a* in the first image 712 that is the second bridge image based on the fourth coordinate value 722*a*. For example, the processor may identify the 2D fifth coordinate value 812*a* corresponding to the 3D fourth coordinate value 722*a*. The processor may use a back projection method, etc. to identify, from the 3D fourth coordinate value 722*a*, the 2D fifth coordinate value 812*a* in the first image 712.

The processor may identify, based on the fifth coordinate value 812*a*, a 3D sixth coordinate value 736*a* corresponding to the second point in the blood vessels in the fourth blood vessel profile data 736. For example, the processor may identify the sixth coordinate value 736*a* in the fourth blood vessel profile data 736, corresponding to the fourth coordinate value 722*a* in the third blood vessel profile data 722, by using the fifth coordinate value 812*a* in the commonly used second bridge image (e.g., the first image 712). In addition, the processor may inject (or substitute) the predicted blood flow characteristic value at the fourth coordinate value 722*a* corresponding to the second point in the blood vessels into the sixth coordinate value 736*a* in the fourth blood vessel profile data 736.

The processor may acquire 3D fifth blood vessel profile data 724 by merging at least the third blood vessel profile data 722 and the fourth blood vessel profile data 736 at least based on the sixth coordinate value 736*a*. In this way, the 3D third blood vessel profile data 722 may be acquired by merging the first blood vessel profile data 732 and the second blood vessel profile data 734 generated based on the second image 714 which is the first bridge image, and the 3D fifth blood vessel profile data 724 may be acquired by merging the third blood vessel profile data 722 and the fourth blood vessel profile data 736 generated (or merged) based on the first image 712 that is the second bridge image. Since this process may be illustrated as images being continuously coupled, it may be referred to as a chain coupling method. In addition, in this case, from the proximal portion of the blood vessels to the second point in the blood vessels, the fifth blood vessel profile data 724 may be acquired by using the third blood vessel profile data 722, and from the second point in the blood vessels to the distal portion of the blood vessels, the fifth blood vessel profile data 724 may be acquired by using the fourth blood vessel profile data 736. In this process, the processor may recalculate the blood flow characteristic value of the blood vessels in the fifth blood vessel profile data 724. For example, since the predicted blood flow characteristic value at the fourth coordinate value 722*a* corresponding to the second point in the blood vessels is injected (or substituted) into the sixth coordinate value 736*a* in the fourth blood vessel profile data 736, the processor may recalculate the blood flow characteristic value by using the injected (or substituted) value as an initial value.

Figure 9:
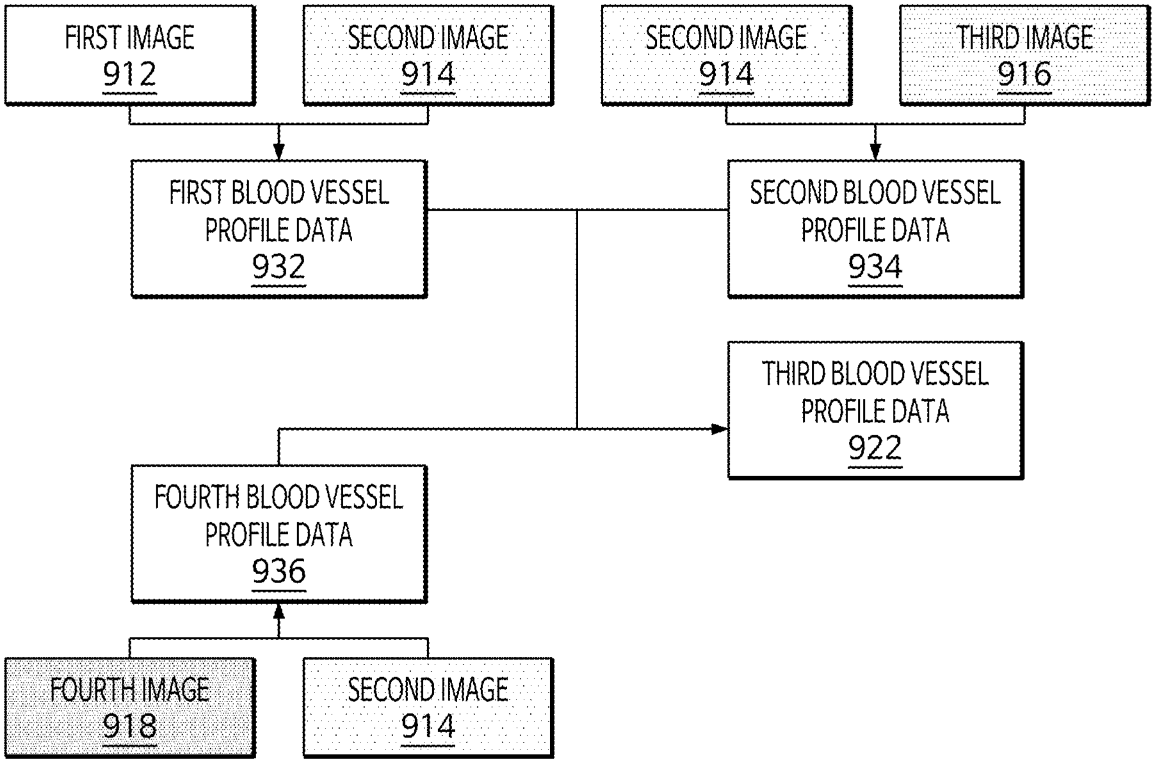
FIG. 9 is a diagram provided to explain a third method for generating 3D blood vessel profile data according to an aspect of the present disclosure.
Figure 10:
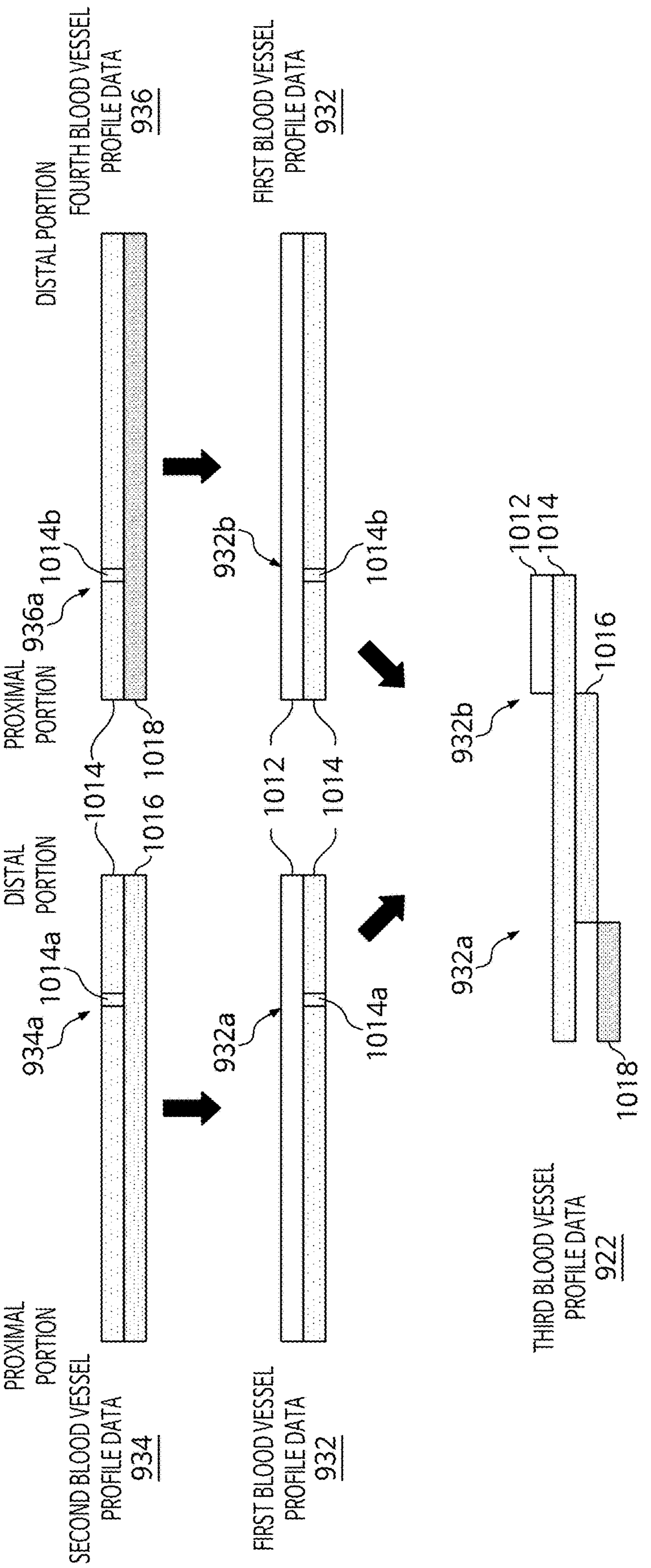
FIG. 10 is a diagram schematically illustrating image information included in the blood vessel profile data by the third method for generating the 3D blood vessel profile data according to an aspect of the present disclosure.

FIG. 9 is a diagram provided to explain a third method for generating 3D blood vessel profile data according to an aspect of the present disclosure, and FIG. 10 is a diagram schematically illustrating image information included in the blood vessel profile data by the third method for generating the 3D blood vessel profile data according to an aspect of the present disclosure. Referring to FIGS. 9 and 10, the processor (e.g., the processor 220 of FIGS. 2 and 3) of the electronic device (e.g., the electronic device 100 of FIGS. 1 and 2) may generate 3D blood vessel profile data 932, 934, 936, and 922 based on a plurality of images 912, 914, 916, and 918 including blood vessels. In FIGS. 9 and 10, a one bridge coupling method as an example of a method for acquiring the blood vessel profile data using four images will be described. In FIG. 10, a plurality of image data 1012, 1014, 1016, and 1018 used for generating the blood vessel profile data 932, 934, 936, and 922 may correspond to the plurality of images 912, 914, 916, and 918, and they are illustrated in the form of straight lines for convenience of explanation. For example, the first image data 1012 may correspond to the first image 912, the second image data 1014 may correspond to the second image 914, the third image data 1016 may correspond to the third image 916, and the fourth image data 1018 may correspond to the fourth image 918.

According to the method (one bridge coupling method) for acquiring the blood vessel profile data, the processor may generate the 3D first blood vessel profile data 932 by using the first image 912 and the second image 914. For example, the processor may generate the first blood vessel profile data 932 by using the first image data 1012 and the second image data 1014. In addition, the processor may generate the 3D second blood vessel profile data 934 by using the second image 914 and the third image 916. For example, the processor may generate the second blood vessel profile data 934 by using the second image data 1014 and the third image data 1016. In addition, the processor may use generate 3D fourth blood vessel profile data 936 by using the second image 914 and the fourth image 918. For example, the processor may generate the fourth blood vessel profile data 936 by using the second image data 1014 and the fourth image data 1018. In this case, the second image 914 may be a bridge image that is commonly used for generating the first blood vessel profile data 932, the second blood vessel profile data 934, and the fourth blood vessel profile data 936.

If the first blood vessel profile data 932, the second blood vessel profile data 934, and the fourth blood vessel profile data 936 are generated by using the bridge image, the processor may acquire the 3D third blood vessel profile data 922 by merging the first blood vessel profile data 932, the second blood vessel profile data 934, and the fourth blood vessel profile data 936. That is, the processor may use the one bridge image to merge three or more blood vessel profile data.

In more detail, the processor may identify a first coordinate value 934*a* corresponding to the first point in the blood vessels in the second blood vessel profile data 934. In addition, the processor may acquire a predicted blood flow characteristic value at the first coordinate value 934*a* corresponding to the first point in the blood vessels. Likewise, the processor may identify a fourth coordinate value 936*a* corresponding to the second point in the blood vessels in the fourth blood vessel profile data 936. The first and second points in the blood vessels may include a boundary point where the identification of the blood vessels can be determined. For example, the first point in the blood vessels may include a boundary point at which a value indicating a degree of identifying a specific region in the blood vessels in the image (e.g., in the second image 914 or the third image 916) used for generating the second blood vessel profile data 934 or the second blood vessel profile data 934 is less than a value specified between the proximal and distal portions of the blood vessels. In addition, the second point in the blood vessels may include a boundary point at which a value indicating the degree of identifying a specific region in the blood vessels in the image (e.g., the second image 914 or the fourth image 918) used for generating the fourth blood vessel profile data 936 or the fourth blood vessel profile data 936 is less than a value specified between the proximal and distal portions of the blood vessels.

The processor may identify a second coordinate value 1014*a* in the second image 914 that is a bridge image based on the first coordinate value 934*a*. For example, the processor may identify a 2D second coordinate value 1014*a* corresponding to the 3D first coordinate value 934*a*. In addition, the processor may identify a fifth coordinate value 1014*b* in the second image 914 that is a bridge image based on the fourth coordinate value 936*a*. For example, the processor may identify the 2D fifth coordinate value 1014*b* corresponding to the 3D fourth coordinate value 936*a*. The processor may use the back projection method, etc. to identify, from the 3D first coordinate value 934*a*, the 2D second coordinate value 1014*a* in the second image 914, and identify, from the 3D fourth coordinate value 936*a*, the 2D fifth coordinate value 1014*b* in the second image 914.

The processor may identify a third coordinate value 932*a* corresponding to the first point in the blood vessels in the first blood vessel profile data 932 based on the second coordinate value 1014*a*. For example, the processor may identify the third coordinate value 932*a* in the first blood vessel profile data 932 corresponding to the first coordinate value 934*a* in the second blood vessel profile data 934 by using the second coordinate value 1014*a* in the commonly used bridge image (e.g., in the second image 914). In addition, the processor may identify a sixth coordinate value 932*b* corresponding to the second point in the blood vessels in the first blood vessel profile data 932 based on the fifth coordinate value 1014*b*. For example, the processor may identify the sixth coordinate value 932*b* in the first blood vessel profile data 932 corresponding to the fourth coordinate value 936*a* in the fourth blood vessel profile data 936 by using the fifth coordinate value 1014*b* in the commonly used bridge image (e.g., the second image 914). In addition, the processor may inject (or substitute) the predicted blood flow characteristic value at the first coordinate value 934*a* corresponding to the first point in the blood vessels into the third coordinate value 932*a* in the first blood vessel profile data 932, and may inject (or substitute) the predicted blood flow characteristic value at the fourth coordinate value 936*a* corresponding to the second point in the blood vessels into the sixth coordinate value 932*b* in the first blood vessel profile data 932.

The processor may acquire the third blood vessel profile data 922 by merging at least the first blood vessel profile data 932, the second blood vessel profile data 934, and the fourth blood vessel profile data 936 at least based on the third coordinate value 932*a* and the sixth coordinate value 932*b*. In this way, the 3D third blood vessel profile data 922 may be acquired by merging the first blood vessel profile data 932, the second blood vessel profile data 934, and the fourth blood vessel profile data 936, which are generated based on one bridge image, that is, the second image 914. In this case, from the proximal portion of the blood vessels to the second point in the blood vessels, the third blood vessel profile data 922 may be acquired by using the fourth blood vessel profile data 936, and from the second point in the blood vessels to the first point in the blood vessels, the third blood vessel profile data 922 may be acquired by using the second blood vessel profile data 934, and from the first point in the blood vessels to the distal portion of the blood vessels, the third blood vessel profile data 922 may be acquired by using the first blood vessel profile data 932. In this process, the processor may recalculate the blood flow characteristic value of the blood vessels in the third blood vessel profile data 922. For example, since the predicted blood flow characteristic value at the first coordinate value 934*a* corresponding to the first point in the blood vessels is injected (or substituted) into the third coordinate value 932*a* in the first blood vessel profile data 932, and the predicted blood flow characteristic value at the fourth coordinate value 936*a* corresponding to the second point in the blood vessels is injected (or substituted) into the sixth coordinate value 932*b* at the first blood vessel profile data 932, the processor may recalculate the blood flow characteristic value by using the injected (or substituted) value as an initial value.

Figure 11:
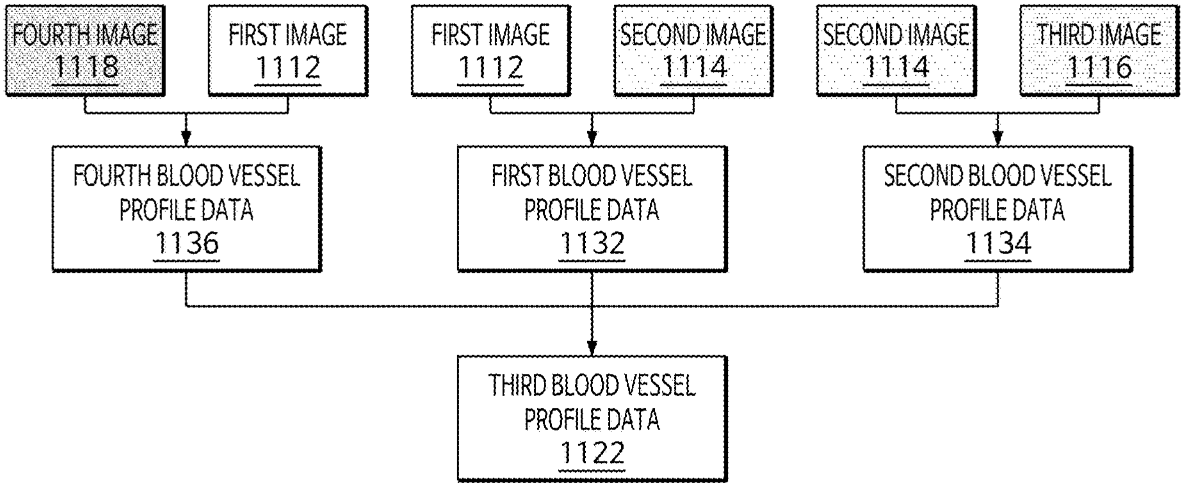
FIG. 11 is a diagram provided to explain a fourth method for generating 3D blood vessel profile data according to an aspect of the present disclosure.
Figure 12:
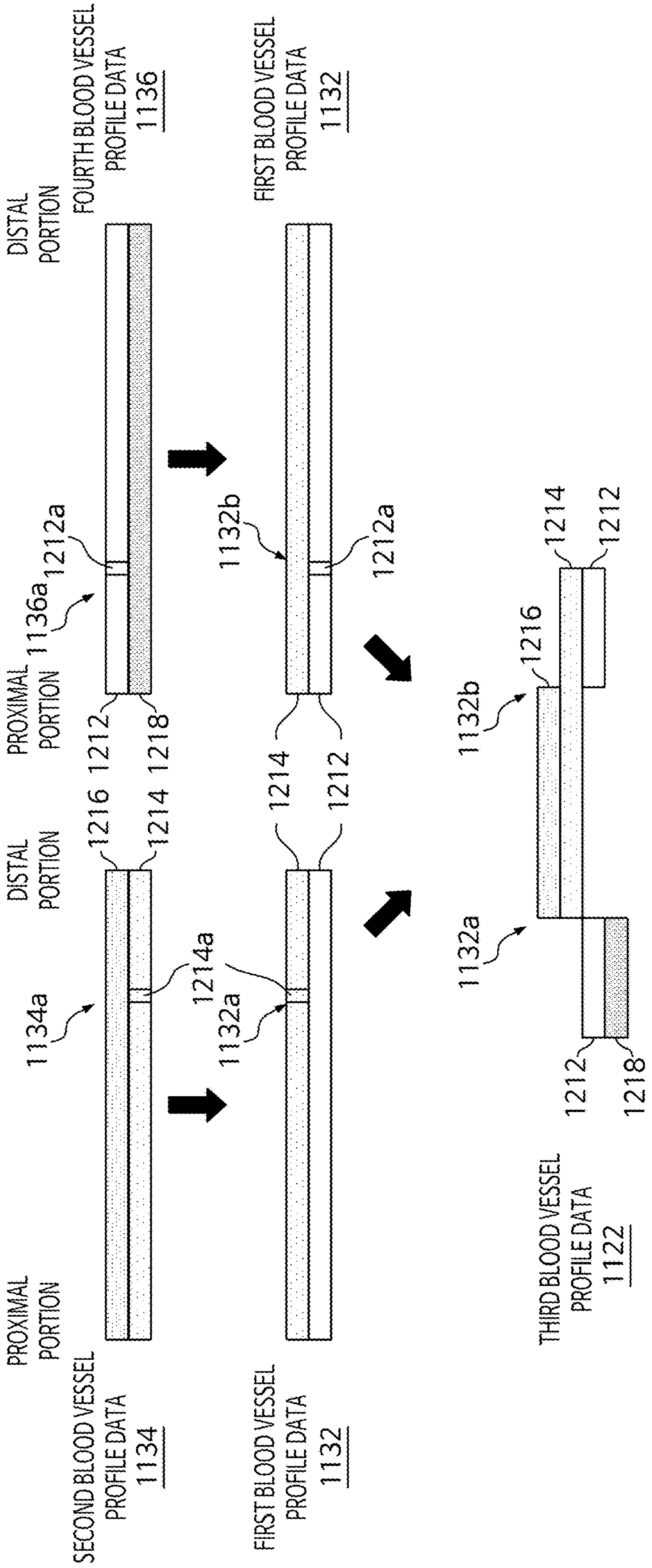
FIG. 12 is a diagram schematically illustrating image information included in the blood vessel profile data by the fourth method for generating the 3D blood vessel profile data according to an aspect of the present disclosure.

FIG. 11 is a diagram provided to explain a fourth method for generating 3D blood vessel profile data according to an aspect of the present disclosure, and FIG. 12 is a diagram schematically illustrating image information included in the blood vessel profile data by the fourth method for generating the 3D blood vessel profile data according to an aspect of the present disclosure. Referring to FIGS. 11 and 12, the processor (e.g., the processor 220 of FIGS. 2 and 3) of the electronic device (e.g., the electronic device 100 of FIGS. 1 and 2) may generate 3D blood vessel profile data 1132, 1134, 1136, and 1122 based on a plurality of images 1112, 1114, 1116, and 1118 including blood vessels. In FIGS. 11 and 12, a side coupling method as an example of a method for acquiring the blood vessel profile data using four images will be described. In FIG. 12, a plurality of image data 1212, 1214, 1216, and 1218 used for generating the blood vessel profile data 1132, 1134, 1136, and 1122 may correspond to the plurality of images 1112, 1114, 1116, and 1118, and they are illustrated in the form of straight lines for convenience of explanation. For example, the first image data 1212 may correspond to the first image 1112, the second image data 1214 may correspond to the second image 1114, the third image data 1216 may correspond to the third image 1116, and the fourth image data 1218 may correspond to the fourth image 1118.

According to the method (side combination method) for acquiring the blood vessel profile data, the processor may generate the 3D first blood vessel profile data 1132 by using the first image 1112 and the second image 1114. For example, the processor may generate the first blood vessel profile data 1132 by using the first image data 1212 and the second image data 1214. In addition, the processor may generate the 3D second blood vessel profile data 1134 by using the second image 1114 and the third image 1116. For example, the processor may generate the second blood vessel profile data 1134 by using the second image data 1214 and the third image data 1216. In addition, the processor may generate the 3D fourth blood vessel profile data 1136 by using the first image 1112 and the fourth image 1118. For example, the processor may generate the fourth blood vessel profile data 1136 by using the first image data 1212 and the fourth image data 1218. In this case, the second image 1114 may be a first bridge image that is commonly used for generating the first blood vessel profile data 1132 and the second blood vessel profile data 1134, and the first image 1112 may be a second bridge image that is commonly used for generating the first blood vessel profile data 1132 and the fourth blood vessel profile data 1136.

If the first blood vessel profile data 1132, the second blood vessel profile data 1134, and the fourth blood vessel profile data 1136 are generated by using the bridge image, the processor may acquire the 3D third blood vessel profile data 1122 by merging the first blood vessel profile data 1132, the second blood vessel profile data 1134, and the fourth blood vessel profile data 1136.

In more detail, the processor may identify a first coordinate value 1134*a* corresponding to a first point in the blood vessels in the second blood vessel profile data 1134. In addition, the processor may acquire a predicted blood flow characteristic value at the first coordinate value 1134*a* corresponding to the first point in the blood vessels. Likewise, the processor may identify a fourth coordinate value 1136*a* corresponding to the second point in the blood vessels in the fourth blood vessel profile data 1136. The first and second points in the blood vessels may include a boundary point where the identification of the blood vessels can be determined. For example, the first point in the blood vessels may include a boundary point at which a value indicating a degree of identifying a specific region in the blood vessels in the image (e.g., in the second image 1114 or the third image 1116) used for generating the second blood vessel profile data 1134 or the second blood vessel profile data 1134 is less than a value specified between the proximal and distal portions of the blood vessels. In addition, the second point in the blood vessels may include a boundary point at which a value indicating a degree of identifying a specific region in the blood vessels in the image (e.g., in the first image 1112 or the fourth image 1118) used for generating the fourth blood vessel profile data 1136 or the fourth blood vessel profile data 1136 is less than a value specified between the proximal and distal portions of the blood vessels.

The processor may identify a second coordinate value 1214*a* in the second image 1114 that is a bridge image based on the first coordinate value 1134*a*. For example, the processor may identify a 2D second coordinate value 1214*a* corresponding to the 3D first coordinate value 1134*a*. In addition, the processor may identify a fifth coordinate value 1212*a* in the first image 1112 that is a bridge image based on the fourth coordinate value 1136*a*. For example, the processor may identify the 2D fifth coordinate value 1212*a* corresponding to the 3D fourth coordinate value 1136*a*. The processor may use the back projection method, etc. to identify, from the 3D first coordinate value 1134*a*, the 2D second coordinate value 1214*a* in the second image 1114, and identify, from the 3D fourth coordinate value 1136*a*, the 2D fifth coordinate value 1212*a* in the first image 1112.

The processor may identify a third coordinate value 1132*a* corresponding to the first point in the blood vessels in the first blood vessel profile data 1132 based on the second coordinate value 1214*a*. For example, the processor may identify the third coordinate value 1132*a* in the first blood vessel profile data 1132 corresponding to the first coordinate value 1134*a* in the second blood vessel profile data 1134, by using the second coordinate value 1214*a* in the commonly used first bridge image (e.g., the second image 1114). In addition, the processor may identify a sixth coordinate value 1132*b* corresponding to the second point in the blood vessels in the first blood vessel profile data 1132 based on the fifth coordinate value 1212*a*. For example, the processor may identify the sixth coordinate value 1132 in the first blood vessel profile data 1132 corresponding to the fourth coordinate value 1136*a* in the fourth blood vessel profile data 1136, by using the fifth coordinate value 1212*a* in the commonly used second bridge image (e.g., the first image 1112). In addition, the processor may inject (or substitute) the predicted blood flow characteristic value at the first coordinate value 1134*a* corresponding to the first point in the blood vessels into the third coordinate value 1132*a* in the first blood vessel profile data 1132, and may inject (or substitute) the predicted blood flow characteristic value at the fourth coordinate value 1136*a* corresponding to the second point in the blood vessels into the sixth coordinate value 1132*b* in the first blood vessel profile data 1132.

The processor may acquire the third blood vessel profile data 1122 by merging at least the first blood vessel profile data 1132, the second blood vessel profile data 1134, and the fourth blood vessel profile data 1136 at least based on the third coordinate value 1132*a* and the sixth coordinate value 1132*b*. In this way, the process involves merging the first blood vessel profile data 1132, the second blood vessel profile data 1134, and the fourth blood vessel profile data 1136 based on the first blood vessel profile data 1132 that is generated based on two bridge images, i.e., the first image 1112 and the second image 1114, and this process may be referred to as the side coupling method because it may be illustrated that the blood vessel profile data (e.g., the second blood vessel profile data 1134 and the fourth blood vessel profile data 1136) on both sides are coupled with the blood vessel profile data (e.g., the first blood vessel profile data 1132) in the center. In addition, in this case, from the proximal portion of the blood vessels to the second point in the blood vessels, the third blood vessel profile data 1122 may be acquired by using the fourth blood vessel profile data 1136, from the second point in the blood vessels to the first point in the blood vessels, the third blood vessel profile data 922 may be acquired by using the second blood vessel profile data 1134, and from the first point in the blood vessels to the distal portion of the blood vessels, the third blood vessel profile data 922 may be acquired by using the first blood vessel profile data 1132. In this process, the processor may recalculate the blood flow characteristic value of the blood vessels in the third blood vessel profile data 1122. For example, since the predicted blood flow characteristic value at the first coordinate value 1134*a* corresponding to the first point in the blood vessels is injected (or substituted) into the third coordinate value 1132*a* in the first blood vessel profile data 1132, and the predicted blood flow characteristic value at the fourth coordinate value 1136*a* corresponding to the second point in the blood vessels is injected (or substituted) into the sixth coordinate value 1132*b* at the first blood vessel profile data 1132, the processor may recalculate the blood flow characteristic value by using the injected (or substituted) value as an initial value.

Figure 13:
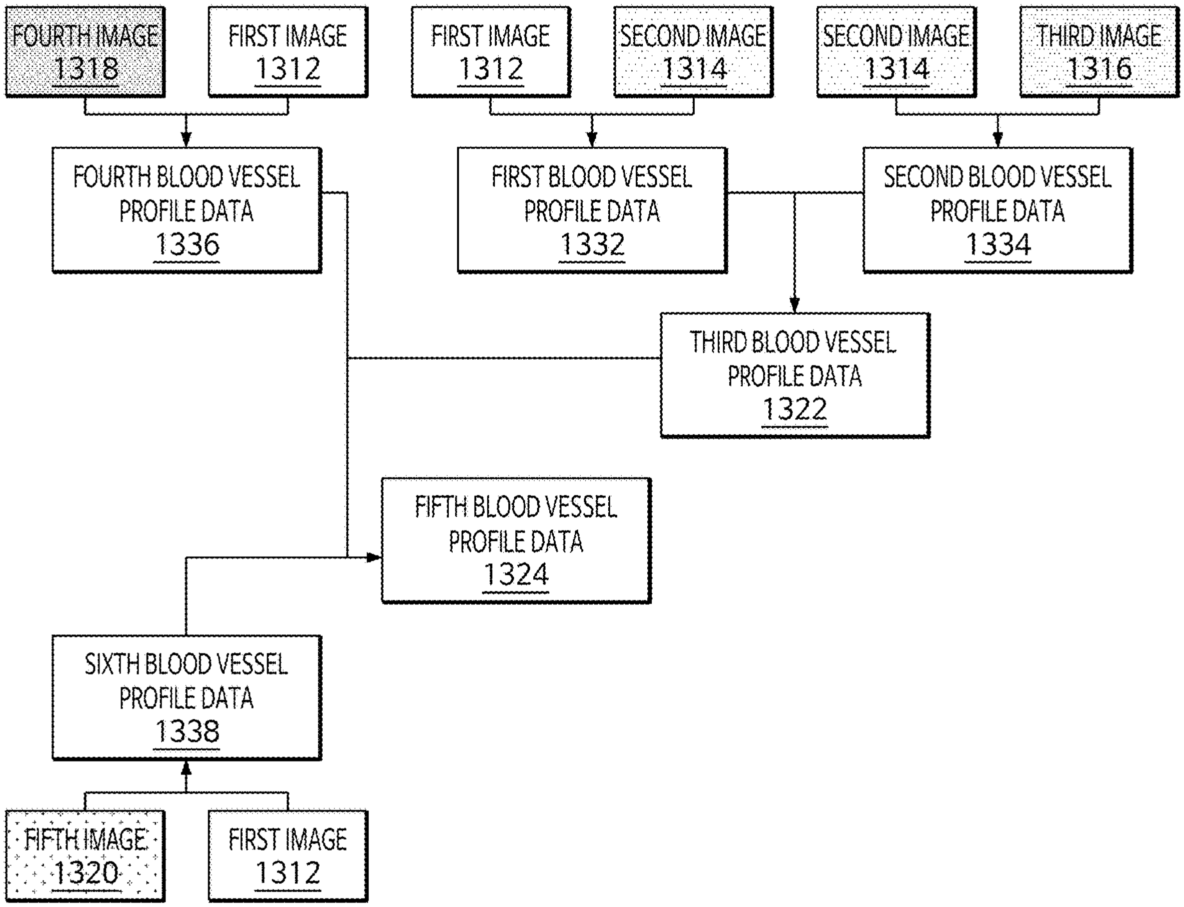
FIG. 13 is a diagram provided to explain a fifth method for generating 3D blood vessel profile data according to an aspect of the present disclosure.

FIG. 13 is a diagram provided to explain a fifth method for generating 3D blood vessel profile data according to an aspect of the present disclosure. Referring to FIG. 13, the processor (e.g., the processor 220 of FIGS. 2 and 3) of the electronic device (e.g., the electronic device 100 of FIGS. 1 and 2) may generate 3D blood vessel profile data 1332, 1334, 1336, 1338, 1322, and 1324 based on a plurality of images 1312, 1314, 1316, 1318, and 1320 including blood vessels. Although FIG. 13 illustrates a method for acquiring blood vessel profile data using five images, the number of images is not limited thereto. The method for acquiring the blood vessel profile data illustrated in FIG. 13 is a method that combines the chain coupling method and the one bridge coupling method and will be described below.

According to the method (method combining the chain coupling method and the one bridge coupling method) for acquiring the blood vessel profile data, the processor may generate the 3D first blood vessel profile data 1332 by using the first image 1312 and the second image 1314. In addition, the processor may generate the 3D second blood vessel profile data 1334 by using the second image 1314 and the third image 1316. In addition, the processor may generate the 3D fourth blood vessel profile data 1336 by using the first image 1312 and the fourth image 1318. In addition, the processor may generate the 3D sixth blood vessel profile data 1338 by using the first image 1312 and the fifth image 1320. In this case, the second image 1314 may be the first bridge image that is commonly used for generating the first blood vessel profile data 1332 and the second blood vessel profile data 1334, and the first image 1312 may be the second bridge image that is commonly used for generating the first blood vessel profile data 1332, the fourth blood vessel profile data 1336, and the sixth blood vessel profile data 1338.

If the first blood vessel profile data 1332 and the second blood vessel profile data 1334 are generated by using the first bridge image, the processor may acquire the 3D third blood vessel profile data 1322 by merging the first blood vessel profile data 1332 and the second blood vessel profile data 1334. The process of acquiring the 3D third blood vessel profile data 1322 by merging the first blood vessel profile data 1332 and the second blood vessel profile data 1334 may be the same as or similar to the process of acquiring the blood vessel profile data described above with reference to FIGS. 4 to 6.

The processor may acquire the 3D fifth blood vessel profile data 1324 by merging the third blood vessel profile data 1322, the fourth blood vessel profile data 1336, and the sixth blood vessel profile data 1338, which are generated (or merged) based on the second bridge image. The process of acquiring the 3D fifth blood vessel profile data 1324 by merging the third blood vessel profile data 1322, the fourth blood vessel profile data 1336, and the sixth blood vessel profile data 1338 may be the same as or similar to the process of acquiring the blood vessel profile data described above with reference to FIGS. 9 and 10.

In more detail, the processor may identify a 3D fourth coordinate value corresponding to the second point in the blood vessels in the third blood vessel profile data 1322. In addition, the processor may identify a 3D seventh coordinate value corresponding to a third point in the blood vessels in the sixth blood vessel profile data 1338. In addition, the processor may acquire a predicted blood flow characteristic value at a fourth coordinate value corresponding to the second point in the blood vessels and a predicted blood flow characteristic value at a seventh coordinate value corresponding to the third point in the blood vessels.

The processor may identify the 2D fifth coordinate value in the first image 1312 that is the second bridge image based on the fourth coordinate value. For example, the processor may identify a 2D fifth coordinate value corresponding to the 3D fourth coordinate value. In addition, the processor may identify the 2D eighth coordinate value in the first image 1312 that is the second bridge image based on the seventh coordinate value. For example, the processor may identify the 2D eighth coordinate value corresponding to the 3D seventh coordinate value. The processor may use the back projection method, etc. to identify, from each of the 3D fourth coordinate value and the seventh coordinate value, the 2D fifth coordinate value and the eighth coordinate value in the first image 1312.

The processor may identify, based on the fifth coordinate value, a 3D sixth coordinate value corresponding to the second point in the blood vessels in the fourth blood vessel profile data 1336. For example, the processor may identify the sixth coordinate value in the fourth blood vessel profile data 1336, corresponding to the fourth coordinate value in the third blood vessel profile data 1322, by using the fifth coordinate value in the commonly used second bridge image (e.g., the first image 1312). In addition, the processor may identify a 3D ninth coordinate value corresponding to a third point in the blood vessels in the fourth blood vessel profile data 1336 based on the eighth coordinate value. For example, the processor may identify the ninth coordinate value in the fourth blood vessel profile data 1336, corresponding to the seventh coordinate value in the sixth blood vessel profile data 1338, by using the eighth coordinate value in the commonly used second bridge image (e.g., the first image 1312). In addition, the processor may inject (or substitute) the predicted blood flow characteristic value at the fourth coordinate value corresponding to the second point in the blood vessels into the sixth coordinate value in the fourth blood vessel profile data 1336, and may inject (or substitute) the predicted blood flow characteristic value at the seventh coordinate value corresponding to the third point in the blood vessels into the ninth coordinate value in the fourth blood vessel profile data 1336.

The processor may acquire the fifth blood vessel profile data 1324 by merging at least the third blood vessel profile data 1322, the fourth blood vessel profile data 1336, and the sixth blood vessel profile data 1338 at least based on the sixth coordinate value and the ninth coordinate value. In addition, the processor may recalculate the blood flow characteristic value of the blood vessels in the fifth blood vessel profile data 1324. For example, since the predicted blood flow characteristic value at the fourth coordinate value corresponding to the second point in the blood vessels is injected (or substituted) into the sixth coordinate value in the fourth blood vessel profile data 1336, and the predicted blood flow characteristic value at the seventh coordinate value corresponding to the third point in the blood vessels is injected (or substituted) into the ninth coordinate value in the fourth blood vessel profile data 1336, the processor may recalculate the blood flow characteristic value by using the injected (or substituted) value as an initial value.

Figure 14:
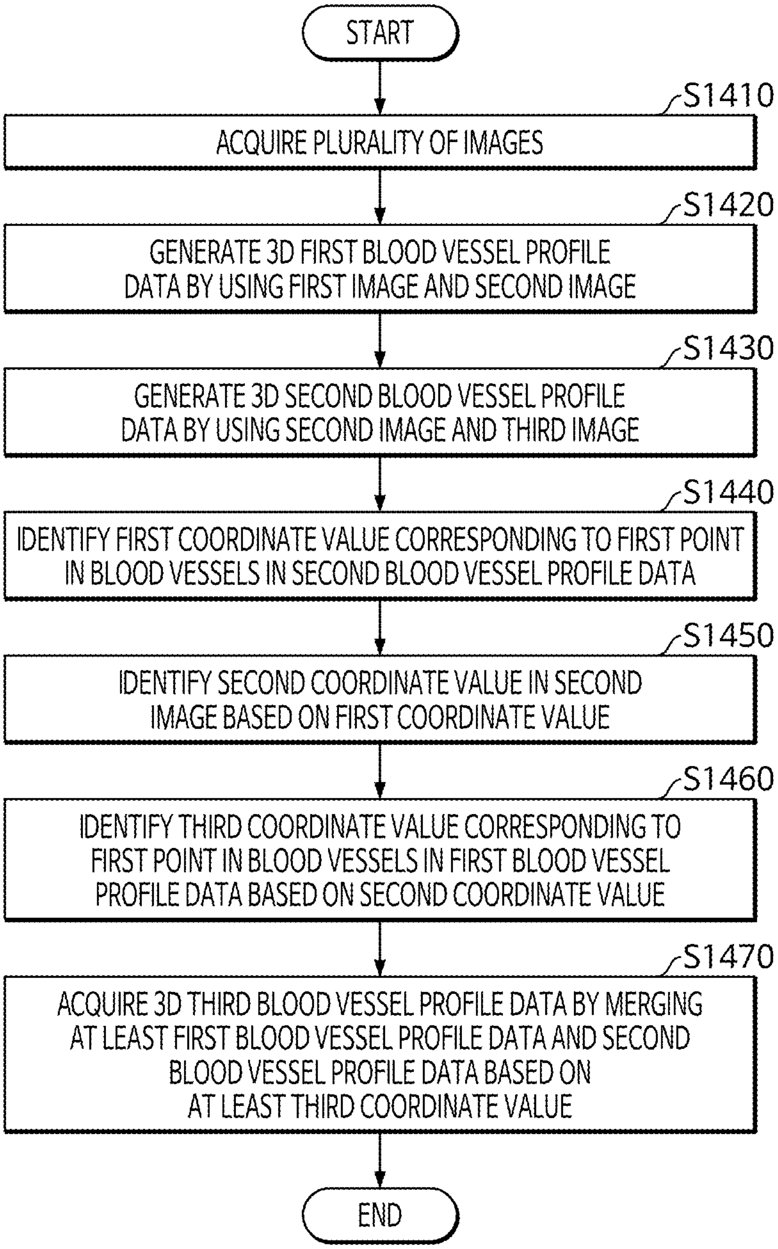
FIG. 14 is a diagram provided to explain a method for generating 3D blood vessel profile data according to an aspect of the present disclosure.

FIG. 14 is a diagram provided to explain a method for generating 3D blood vessel profile data according to an aspect of the present disclosure. Referring to FIG. 14, the processor (e.g., the processor 220 of FIGS. 2 and 3) of the electronic device (e.g., the electronic device 100 of FIGS. 1 and 2) may acquire a plurality of images, at S1410. For example, the processor may acquire a plurality of images including blood vessels (e.g., the plurality of images 110 of FIG. 1). The plurality of images may include a plurality of angiographic images acquired at different viewing angles.

At S1420, the processor may generate 3D first blood vessel profile data by using the first image and the second image. For example, the processor may generate 3D first blood vessel profile data by using the first image and the second image of the plurality of images.

The processor may generate the 3D second blood vessel profile data by using the second image and the third image, at S1430. For example, the processor may generate 3D second blood vessel profile data by using the second image and a third image of the plurality of images. In this case, the second image may be a bridge image that is commonly used for generating the first blood vessel profile data and the second blood vessel profile data.

The processor may identify a first coordinate value corresponding to a first point in the blood vessels in the second blood vessel profile data, at S1440. For example, based on the assumption that the proximal portion of the blood vessels is the origin in the 3D coordinate system in the second blood vessel profile data, the processor may identify the first coordinate value corresponding to the first point in the blood vessels. In addition, the processor may acquire a predicted blood flow characteristic value at a first coordinate value corresponding to the first point in the blood vessels. The first point in the blood vessels may include a boundary point where the identification of the blood vessels can be determined. For example, the first point in the blood vessels may include a boundary point at which a value indicating a degree of identifying a specific region in the blood vessels in the image (e.g., in the second image or the third image) used for generating the second blood vessel profile data 434 or the second blood vessel profile data 434 is less than a value specified between the proximal and distal portions of the blood vessels.

The processor may identify the second coordinate value in the second image based on the first coordinate value, at S1450. That is, the processor may identify a second coordinate value corresponding to the first coordinate value in the second image that is a bridge image. For example, the processor may identify a 2D second coordinate value corresponding to the 3D first coordinate value. The processor may use the back projection method, etc. to identify, from the 3D first coordinate value, the 2D second coordinate value in the second image.

The processor may identify a third coordinate value corresponding to the first point in the blood vessels in the first blood vessel profile data based on the second coordinate value, at S1460. For example, the processor may use the second coordinate value in the second image that is a bridge image to identify the third coordinate value in the first blood vessel profile data corresponding to the first coordinate value in the second blood vessel profile data. In addition, the processor may inject (or substitute) the predicted blood flow characteristic value at the first coordinate value corresponding to the first point in the blood vessels into the third coordinate value in the first blood vessel profile data.

The processor may acquire 3D third blood vessel profile data by merging at least the first blood vessel profile data and the second blood vessel profile data at least based on the third coordinate value, at S1470. For example, the processor may acquire 3D third blood vessel profile data by merging the first blood vessel profile data and the second blood vessel profile data, which are generated based on the second image that is a bridge image. In this case, from the proximal portion of the blood vessels to the first point in the blood vessels, the third blood vessel profile data may be acquired by using the second blood vessel profile data, and from the first point in the blood vessels to the distal portion of the blood vessels, the third blood vessel profile data may be acquired by using the first blood vessel profile data. In this process, the processor may recalculate the blood flow characteristic value of the blood vessels in the third blood vessel profile data. For example, since the predicted blood flow characteristic value at the first coordinate value corresponding to the first point in the blood vessels is injected (or substituted) into the third coordinate value in the first blood vessel profile data, the processor may recalculate the blood flow characteristic value by using the injected (or substituted) value as an initial value. Accordingly, from the proximal portion of the blood vessels to the first point in the blood vessels, the blood flow characteristic value of the blood vessels may correspond to the first blood flow characteristic value predicted by using the second blood vessel profile data, and from the first point in the blood vessels to the distal portion of the blood vessels, the blood flow characteristic value of the blood vessels may correspond to the second blood flow characteristic value predicted by using the first blood vessel profile data with the first blood flow characteristic value corresponding to the first point in the blood vessels as an initial value.

The flowcharts and aspects described above are merely examples, and may be implemented differently depending on aspects. For example, in some aspects, the order of respective operations may be changed, some of the operations may be repeatedly performed, some may be omitted, or some may be added.

Figure 15:
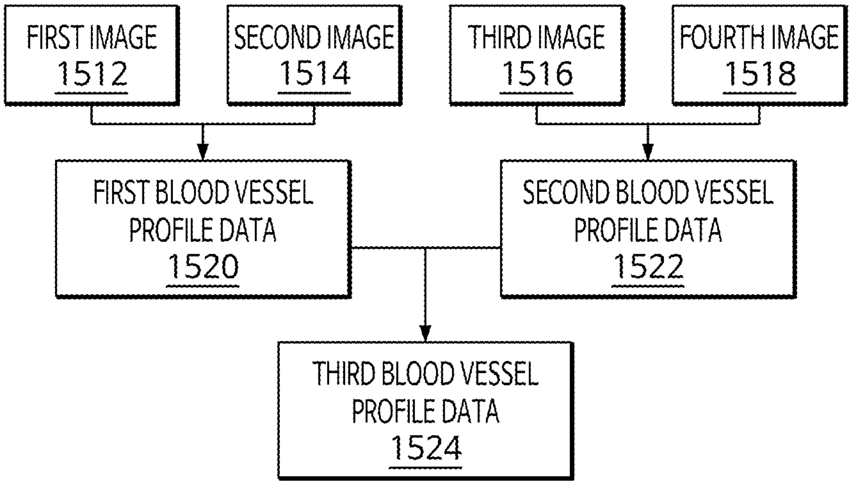
FIG. 15 is a diagram provided to explain a first method for generating 3D blood vessel profile data according to other aspects.

FIG. 15 is a diagram provided to explain a first method for generating 3D blood vessel profile data according to other aspects. Referring to FIG. 15, the processor (e.g., the processor 220 of FIGS. 2 and 3) of the electronic device (e.g., the electronic device 100 of FIGS. 1 and 2) may generate 3D blood vessel profile data 1520, 1522, and 1524 based on a plurality of images 1512, 1514, 1516, and 1518 including blood vessels. FIG. 15 illustrates that the 3D blood vessel profile data is generated by using the first image 1512 and the second image 1514 included in a first set of images, and the third image 1516 and the fourth image 1518 included in a second set of images, but aspects are not limited thereto. For example, the first set of images may include one or three or more images, and the second set of images may include one or three or more images.

The electronic device may generate the 3D first blood vessel profile data 1520 by using the first set of images including the first image 1512 and the second image 1514. In addition, the electronic device may generate the 3D second blood vessel profile data 1522 by using the second set of images including the third image 1516 and the fourth image 1518. In this case, the first image 1512 and the second image 1514 included in the first set of images may refer to angiographic images acquired at different viewing angles. In addition, the third image 1516 and the fourth image 1518 included in the second set of images may refer to angiographic images acquired at different viewing angles. Additionally or alternatively, each of the first image 1512 and the second image 1514 included in the first set of images and the third image 1516 and the fourth image 1518 included in the second set of images may refer to angiographic images acquired at different viewing angles.

The electronic device may generate the 3D third blood vessel profile data 1524 by merging at least the 3D first blood vessel profile data 1520 and the 3D second blood vessel profile data 1522. To this end, the electronic device may identify a first coordinate value indicating a common point based on at least one of the first set of images and at least one of the second set of images. A second coordinate value in the first blood vessel profile data 1520 corresponding to the common point may be identified based on the identified first coordinate value. In addition, a third coordinate value in the second blood vessel profile data 1522 corresponding to the common point may be identified based on the identified first coordinate value. The common point may refer to any point in the blood vessels that indicates the same region or point in at least two images, and may, for example, represent a branch, but is not limited thereto.

The electronic device may output at least one of the first set of images and at least one of the second set of images to identify the first coordinate value indicating the common point. For example, the second image 1514 of the first set of images and the third image 1516 of the second set of images may be output or displayed through an output device (e.g., a display, etc.) of the electronic device. The electronic device may receive a user input for a common point in the second image 1514 and the third image 1516 through the input device (e.g., a touch screen, a mouse, a keyboard, etc.) of the electronic device. The first coordinate value may be identified based on the user input.

Additionally or alternatively, the electronic device may input at least one of the first set of images and at least one of the second set of images to a Common Image Point (CIP) extraction model to automatically detect a common point. The CIP extraction model may refer to any known algorithm and/or artificial neural network model that receives at least two images and extracts a common point in the two images. For example, the CIP extraction model may be an artificial neural network model trained to extract at least one branch in the blood vessels as a common point in at least two received images including blood vessels, but is not limited thereto.

A blood flow characteristic value in the third blood vessel profile data 1524 generated as described above may be predicted and provided to the user. The common point may include a boundary point at which a value indicating a degree of identifying a specific region of the blood vessels in the image including the common point is less than a specified value between the proximal and distal portions of the blood vessels. In this case, the blood flow characteristic value from the proximal portion of the blood vessels to the common point in the blood vessels may correspond to the first blood flow characteristic value predicted by using the first blood vessel profile data 1520 or the second blood vessel profile data 1522. In addition, the blood flow characteristic value from the common point in the blood vessels to the distal portion of the blood vessels may correspond to the second blood flow prediction value predicted by using the blood vessel profile data not used for the first blood flow characteristic value, using the first blood flow characteristic value corresponding to the common point in the blood vessels as a baseline value.

Figure 16:
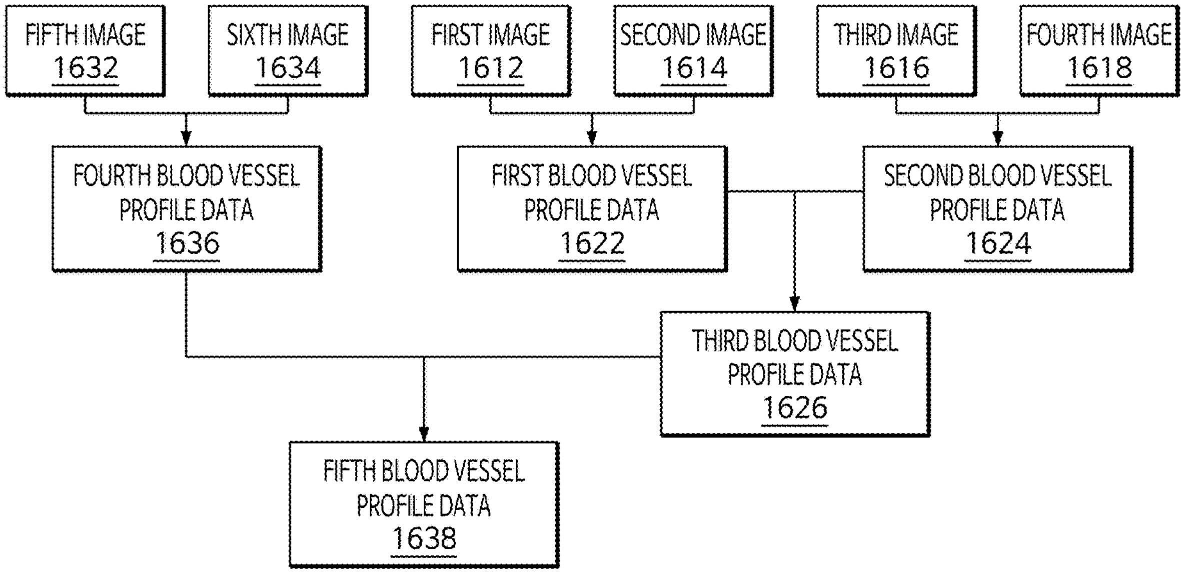
FIG. 16 is a diagram provided to explain a second method for generating 3D blood vessel profile data according to other aspects.

FIG. 16 is a diagram provided to explain a second method for generating 3D blood vessel profile data according to other aspects. Referring to FIG. 16, the processor (e.g., the processor 220 of FIGS. 2 and 3) of the electronic device (e.g., the electronic device 100 of FIGS. 1 and 2) may generate 3D blood vessel profile data 1622, 1624, 1626, 1636, and 1638 based on a plurality of images 1612, 1614, 1614, 1616, 1618, 1632, and 1634 including blood vessels. Each of the first to fourth images 1612, 1614, 1616, and 1618 of FIG. 16 may correspond to the first to fourth images 1512, 1514, 1516, and 1518 of FIG. 15. Likewise, each of the first to third blood vessel profile data 1622, 1624, and 1626 of FIG. 16 may correspond to the first to third blood vessel profile data 1520, 1522, and 1524 of FIG. 15. A chain coupling method based on a common point will be described below as an example of a method for generating blood vessel profile data using six images with reference to FIG. 16, in which components or operations overlapping with FIG. 15 will be omitted and the differences from FIG. 15 will be mainly described.

The electronic device may generate the 3D fourth blood vessel profile data 1636 by using a third set of images including the fifth image 1632 and the sixth image 1634. FIG. 16 illustrates that 3D blood vessel profile data is generated by using the fifth image 1632 and the sixth image 1634 included in the third set of images, but aspects are not limited thereto. For example, the third set of images may include one or more images. In addition, the fifth image 1632 and the sixth image 1634 included in the third set of images may refer to angiographic images acquired at different viewing angles.

The electronic device may identify, based on at least one of the third set of images, a fourth coordinate value indicating the same point as the common point used for generating the third blood vessel profile data 1626. For example, a user input with respect to a coordinate value corresponding to the common point in the sixth image 1634 may be received. Additionally or alternatively, the electronic device may input at least one of the third set of images together with at least one of the first set of images and at least one of the second set of images to the CIP extraction model described in FIG. 15 to identify the common point.

A fifth coordinate value in the fourth blood vessel profile data 1636 corresponding to the common point may be identified based on the identified fourth coordinate value. The electronic device may acquire the 3D fifth blood vessel profile data by merging the 3D third blood vessel profile data 1626 and the 3D fourth blood vessel profile data 1636 at least based on the fifth coordinate value.

Figure 17:
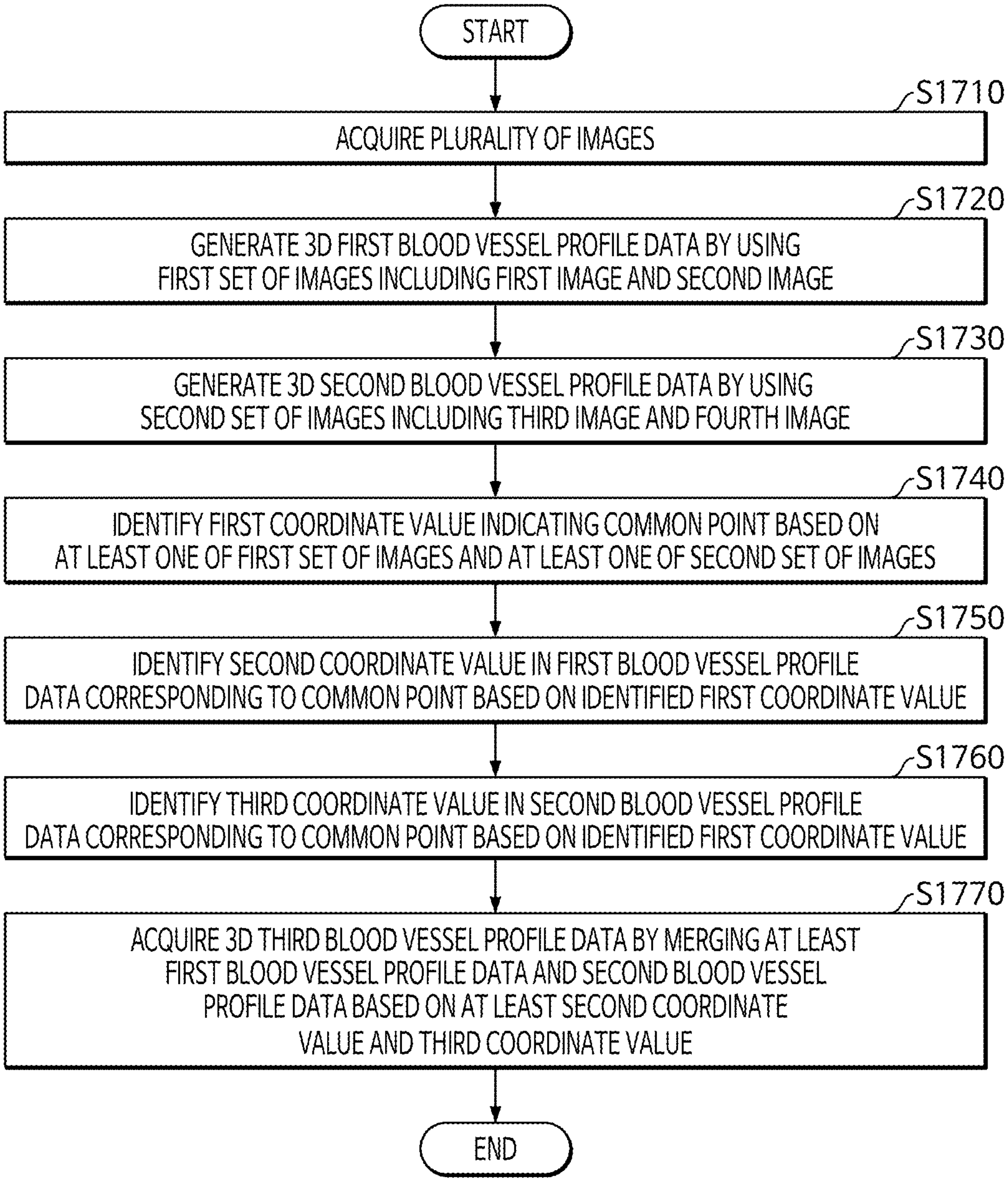
FIG. 17 is a diagram provided to explain a method for generating 3D blood vessel profile data according to other aspects.

FIG. 17 is a diagram provided to explain a method for generating 3D blood vessel profile data according to other aspects. Referring to FIG. 17, the processor of the electronic device (e.g., the electronic device 100 of FIGS. 1 and 2) (e.g., the processor 220 of FIGS. 2 and 3) may acquire a plurality of images, at S1710. For example, the processor may acquire a plurality of images including blood vessels (e.g., the plurality of images 110 of FIG. 1). The plurality of images may include a plurality of angiographic images acquired at different viewing angles.

The processor may generate 3D first blood vessel profile data by using a first set of images including a first image and a second image of the plurality of images, at S1720. In addition, the processor may generate 3D second blood vessel profile data by using a second set of images including a third image and a fourth image of the plurality of images, at S1730.

The processor may identify a first coordinate value indicating a common point, based on at least one of the first set of images and at least one of the second set of images, at S1740. To this end, the processor may output at least one of the first set of images and at least one of the second set of images. The processor may receive a user input for a common point in at least one of the first set of images and at least one of the second set of images which are output, and identify the first coordinate value based on the received user input. Additionally or alternatively, the processor may input at least one of the first set of images and at least one of the second set of images into the CIP extraction model to automatically detect a common point and identify the first coordinate value based on the detected common point.

The processor may identify a second coordinate value in the first blood vessel profile data corresponding to the common point based on the identified first coordinate value, at S1750. In addition, the processor may identify a third coordinate value in the second blood vessel profile data corresponding to the common point based on the identified first coordinate value, at S1760. The processor may acquire 3D third blood vessel profile data by merging at least the first blood vessel profile data and the second blood vessel profile data based on the second coordinate value and the third coordinate value, at S1770.

Additionally, the processor may generate 3D fourth blood vessel profile data by using a third set of images including a fifth image and a sixth image of the plurality of images. In this case, a fourth coordinate value indicating a common point may be identified based on at least one of the third set of images. The processor may identify the fifth coordinate value in the fourth blood vessel profile data corresponding to the common point based on the identified fourth coordinate value. The processor may acquire 3D fifth blood vessel profile data by merging at least the third blood vessel profile data and the fourth blood vessel profile data at least based on the fifth coordinate value.

According to an aspect of the present disclosure, a method for generating three-dimensional blood vessel profile data may be performed by at least one processor and may comprise acquiring a plurality of images including blood vessels, generating three-dimensional first blood vessel profile data by using a first set of images including a first image and a second image of the plurality of images, generating three-dimensional second blood vessel profile data by using a second set of images including a third image and a fourth image of the plurality of images, identifying a first coordinate value indicating a common point based on at least one of the first set of images and at least one of the second set of images, identifying a second coordinate value in the first blood vessel profile data corresponding to the common point based on the identified first coordinate value, identifying a third coordinate value in the second blood vessel profile data corresponding to the common point based on the identified first coordinate value, and acquiring three-dimensional third blood vessel profile data by merging at least the first blood vessel profile data and the second blood vessel profile data at least based on the second coordinate value and the third coordinate value.

According to an aspect of the present disclosure, the plurality of images may include a plurality of angiographic images acquired at different viewing angles.

According to an aspect of the present disclosure, the identifying the first coordinate value indicating the common point may include outputting at least one of the first set of images and at least one of the second set of images, receiving a user input for the common point in the at least one of the first set of images and the at least one of the second set of images that are output, and identifying the first coordinate value based on the received user input.

According to an aspect of the present disclosure, the identifying the first coordinate value indicating the common point may include inputting the at least one of the first set of images and the at least one of the second set of images into a Common Image Point (CIP) extraction model to automatically detect the common point, and identifying the first coordinate value based on the detected common point.

According to an aspect of the present disclosure, the method may further comprise generating three-dimensional fourth blood vessel profile data by using a third set of images including a fifth image and a sixth image of the plurality of images, identifying a fourth coordinate value indicating the common point based on at least one of the third set of images, identifying a fifth coordinate value in the fourth blood vessel profile data corresponding to the common point based on the identified fourth coordinate value, and acquiring three-dimensional fifth blood vessel profile data by merging at least the third blood vessel profile data and the fourth blood vessel profile data at least based on the fifth coordinate value.

According to an aspect of the present disclosure, a method for generating three-dimensional blood vessel profile data may be performed by at least one processor and may comprise acquiring a plurality of images including blood vessels, generating three-dimensional first blood vessel profile data by using a first image and a second image of the plurality of images, generating three-dimensional second blood vessel profile data by using the second image and a third image of the plurality of images, identifying a first coordinate value corresponding to a first point in the blood vessels in the second blood vessel profile data, identifying a second coordinate value in the second image based on the first coordinate value, identifying a third coordinate value corresponding to the first point in the blood vessels in the first blood vessel profile data based on the second coordinate value, and acquiring three-dimensional third blood vessel profile data by merging at least the first blood vessel profile data and the second blood vessel profile data at least based on the third coordinate value.

According to an aspect of the present disclosure, the plurality of images may include a plurality of angiographic images acquired at different viewing angles.

According to an aspect of the present disclosure, the first point in the blood vessels may include a boundary point at which a value indicating a degree of identifying a specific region in the blood vessels in the third image is less than a value specified between proximal and distal portions of the blood vessels.

According to an aspect of the present disclosure, the method may further comprise predicting a blood flow characteristic value of the blood vessels by using the third blood vessel profile data, wherein, from a proximal portion of the blood vessels to the first point in the blood vessels, the blood flow characteristic value may correspond to a first blood flow characteristic value predicted by using the second blood vessel profile data, and from the first point in the blood vessels to a distal portion of the blood vessels, the blood flow characteristic value may correspond to a second blood flow characteristic value predicted by using the first blood vessel profile data with the first blood flow characteristic value corresponding to the first point in the blood vessels as an initial value.

According to an aspect of the present disclosure, the method may further comprise generating three-dimensional fourth blood vessel profile data by using the first image and a fourth image of the plurality of images, identifying a third-dimensional fourth coordinate value corresponding to a second point in the blood vessels in the third blood vessel profile data, identifying a two-dimensional fifth coordinate value in the first image based on the fourth coordinate value, identifying a three-dimensional sixth coordinate value corresponding to the second point in the blood vessels in the fourth blood vessel profile data based on the fifth coordinate value, and acquiring three-dimensional fifth blood vessel profile data by merging at least the third blood vessel profile data and the fourth blood vessel profile data at least based on the sixth coordinate value.

According to an aspect of the present disclosure, the method may further comprise generating three-dimensional sixth blood vessel profile data by using the first image and a fifth image of the plurality of images, identifying a three-dimensional seventh coordinate value corresponding to a third point in the blood vessels in the sixth blood vessel profile data, identifying a two-dimensional eighth coordinate value in the first image based on the seventh coordinate value, and identifying a three-dimensional ninth coordinate value corresponding to the third point in the blood vessels in the fourth blood vessel profile data based on the eighth coordinate value, wherein the acquiring the fifth blood vessel profile data may include acquiring the fifth blood vessel profile data by merging at least the third blood vessel profile data, the fourth blood vessel profile data, and the sixth blood vessel profile data at least based on the sixth coordinate value and the ninth coordinate value.

According to an aspect of the present disclosure, the method may further comprise generating three-dimensional fourth blood vessel profile data by using the second image and a fourth image of the plurality of images, identifying a three-dimensional fourth coordinate value corresponding to a second point in the blood vessels in the fourth blood vessel profile data, identifying a two-dimensional fifth coordinate value in the second image based on the fourth coordinate value, and identifying a three-dimensional sixth coordinate value corresponding to the second point in the blood vessels in the first blood vessel profile data based on the fifth coordinate value, wherein the acquiring the third blood vessel profile data may include acquiring the third blood vessel profile data by merging at least the first blood vessel profile data, the second blood vessel profile data, and the fourth blood vessel profile data at least based on the third coordinate value and the sixth coordinate value.

According to an aspect of the present disclosure, the method may further comprise generating three-dimensional fourth blood vessel profile data by using the first image and a fourth image of the plurality of images, identifying a three-dimensional fourth coordinate value corresponding to a second point in the blood vessels in the fourth blood vessel profile data, identifying a two-dimensional fifth coordinate value in the first image based on the fourth coordinate value, identifying a three-dimensional sixth coordinate value corresponding to the second point in the blood vessels in the first blood vessel profile data based on the fifth coordinate value, wherein the acquiring the third blood vessel profile data may include acquiring the third blood vessel profile data by merging at least the first blood vessel profile data, the second blood vessel profile data, and the fourth blood vessel profile data at least based on the third coordinate value and the sixth coordinate value.

According to an aspect of the present disclosure, an electronic device may comprise a memory and one or more processors connected to the memory and configured to execute one or more computer-readable programs included in the memory, wherein the one or more programs may include instructions for acquiring a plurality of images including blood vessels, generating three-dimensional first blood vessel profile data by using a first set of images including a first image and a second image of the plurality of images, generating three-dimensional second blood vessel profile data by using a second set of images including a third image and a fourth image of the plurality of images, identifying a first coordinate value indicating a common point based on at least one of the first set of images and at least one of the second set of images, identifying a second coordinate value in the first blood vessel profile data corresponding to the common point based on the identified first coordinate value, identifying a third coordinate value in the second blood vessel profile data corresponding to the common point based on the identified first coordinate value, and acquiring three-dimensional third blood vessel profile data by merging at least the first blood vessel profile data and the second blood vessel profile data at least based on the second coordinate value and the third coordinate value.

According to an aspect of the present disclosure, the plurality of images may include a plurality of angiographic images acquired at different viewing angles.

According to an aspect of the present disclosure, the one or more programs may further include instructions for outputting at least one of the first set of images and at least one of the second set of images, receiving a user input for the common point in the at least one of the first set of images and the at least one of the second set of images that are output, and identifying the first coordinate value based on the received user input.

According to an aspect of the present disclosure, the one or more programs may further include instructions for inputting the at least one of the first set of images and the at least one of the second set of images into a Common Image Point (CIP) extraction model to automatically detect the common point, and identifying the first coordinate value based on the detected common point.

According to an aspect of the present disclosure, the one or more programs may further include instructions for generating three-dimensional fourth blood vessel profile data by using a third set of images including a fifth image and a sixth image of the plurality of images, identifying a fourth coordinate value indicating the common point based on at least one of the third set of images, identifying a fifth coordinate value in the fourth blood vessel profile data corresponding to the common point based on the identified fourth coordinate value, and acquiring three-dimensional fifth blood vessel profile data by merging at least the third blood vessel profile data and the fourth blood vessel profile data at least based on the fifth coordinate value.

According to an aspect of the present disclosure, an electronic device may comprise a memory and one or more processors connected to the memory and configured to execute one or more computer-readable programs included in the memory, wherein the one or more programs may include instructions for acquiring a plurality of images including blood vessels, generating three-dimensional first blood vessel profile data by using a first image and a second image of the plurality of images, generating three-dimensional second blood vessel profile data by using the second image and a third image of the plurality of images, identifying a first coordinate value corresponding to a first point in the blood vessels in the second blood vessel profile data, identifying a second coordinate value in the second image based on the first coordinate value, identifying a third coordinate value corresponding to the first point in the blood vessels in the first blood vessel profile data based on the second coordinate value, and acquiring three-dimensional third blood vessel profile data by merging at least the first blood vessel profile data and the second blood vessel profile data at least based on the third coordinate value.

According to an aspect of the present disclosure, the plurality of images may include a plurality of angiographic images acquired at different viewing angles.

According to an aspect of the present disclosure, the first point in the blood vessels may include a boundary point at which a value indicating a degree of identifying a specific region in the blood vessels in the third image is less than a value specified between proximal and distal portions of the blood vessels.

According to an aspect of the present disclosure, the one or more programs may further include instructions for predicting a blood flow characteristic value of the blood vessels by using the third blood vessel profile data, and the blood flow characteristic value may correspond to a first blood flow characteristic value predicted by using the second blood vessel profile data from a proximal portion of the blood vessels to the first point in the blood vessels, and the blood flow characteristic value may correspond to a second blood flow characteristic value predicted by using the first blood vessel profile data with the first blood flow characteristic value corresponding to the first point in the blood vessels as an initial value from the first point in the blood vessels to a distal portion of the blood vessels.

According to an aspect of the present disclosure, the one or more programs may further include instructions for generating three-dimensional fourth blood vessel profile data by using the first image and a fourth image of the plurality of images, identifying a third-dimensional fourth coordinate value corresponding to a second point in the blood vessels in the third blood vessel profile data, identifying a two-dimensional fifth coordinate value in the first image based on the fourth coordinate value, identifying a three-dimensional sixth coordinate value corresponding to the second point in the blood vessels in the fourth blood vessel profile data based on the fifth coordinate value, and acquiring three-dimensional fifth blood vessel profile data by merging at least the third blood vessel profile data and the fourth blood vessel profile data at least based on the sixth coordinate value.

According to an aspect of the present disclosure, the one or more programs may further include instructions for generating three-dimensional sixth blood vessel profile data by using the first image and a fifth image of the plurality of images, identifying a three-dimensional seventh coordinate value corresponding to a third point in the blood vessels in the sixth blood vessel profile data, identifying a two-dimensional eighth coordinate value in the first image based on the seventh coordinate value, and identifying a three-dimensional ninth coordinate value corresponding to the third point in the blood vessels in the fourth blood vessel profile data based on the eighth coordinate value, and the acquiring the fifth blood vessel profile data may include acquiring the fifth blood vessel profile data by merging at least the third blood vessel profile data, the fourth blood vessel profile data, and the sixth blood vessel profile data at least based on the sixth coordinate value and the ninth coordinate value.

According to an aspect of the present disclosure, the one or more programs may further include instructions for generating three-dimensional fourth blood vessel profile data by using the second image and a fourth image of the plurality of images, identifying a three-dimensional fourth coordinate value corresponding to a second point in the blood vessels in the fourth blood vessel profile data, identifying a two-dimensional fifth coordinate value in the second image based on the fourth coordinate value, and identifying a three-dimensional sixth coordinate value corresponding to the second point in the blood vessels in the first blood vessel profile data based on the fifth coordinate value, and the acquiring the third blood vessel profile data may include acquiring the third blood vessel profile data by merging at least the first blood vessel profile data, the second blood vessel profile data, and the fourth blood vessel profile data at least based on the third coordinate value and the sixth coordinate value.

According to an aspect of the present disclosure, the one or more programs may further include instructions for generating three-dimensional fourth blood vessel profile data by using the first image and a fourth image of the plurality of images, identifying a three-dimensional fourth coordinate value corresponding to a second point in the blood vessels in the fourth blood vessel profile data, identifying a two-dimensional fifth coordinate value in the first image based on the fourth coordinate value, identifying a three-dimensional sixth coordinate value corresponding to the second point in the blood vessels in the first blood vessel profile data based on the fifth coordinate value, and the acquiring the third blood vessel profile data may include acquiring the third blood vessel profile data by merging at least the first blood vessel profile data, the second blood vessel profile data, and the fourth blood vessel profile data at least based on the third coordinate value and the sixth coordinate value.

The flowchart and description above are merely examples and may be implemented differently in some examples. For example, in some examples, the order of respective steps may be changed, some steps may be repeatedly performed, some steps may be omitted, or some steps may be added.

The method described above may be provided as a computer program stored in a computer-readable recording medium for execution on a computer. The medium may be a type of medium that continuously stores a program executable by a computer, or temporarily stores the program for execution or download. In addition, the medium may be a variety of recording means or storage means having a single piece of hardware or a combination of several pieces of hardware, and is not limited to a medium that is directly connected to any computer system, and accordingly, may be present on a network in a distributed manner. An example of the medium includes a medium configured to store program instructions, including a magnetic medium such as a hard disk, a floppy disk, and a magnetic tape, an optical medium such as a CD-ROM and a DVD, a magnetic-optical medium such as a floptical disk, and a ROM, a RAM, a flash memory, etc. In addition, other examples of the medium may include an app store that distributes applications, a site that supplies or distributes various software, and a recording medium or a storage medium managed by a server.

The methods, operations, or techniques of the present disclosure may be implemented by various means. For example, these techniques may be implemented in hardware, firmware, software, or a combination thereof. Those skilled in the art will further appreciate that various illustrative logical blocks, modules, circuits, and algorithm steps described in connection with the disclosure herein may be implemented in electronic hardware, computer software, or combinations of both. To clearly illustrate this interchangeability of hardware and software, various illustrative components, blocks, modules, circuits, and steps have been described above generally in terms of their functionality. Whether such a function is implemented as hardware or software varies depending on design requirements imposed on the particular application and the overall system. Those skilled in the art may implement the described functions in varying ways for each particular application, but such implementation should not be interpreted as causing a departure from the scope of the present disclosure.

In a hardware implementation, processing units used to perform the techniques may be implemented in one or more ASICs, DSPs, digital signal processing devices (DSPDs), programmable logic devices (PLDs), field programmable gate arrays (FPGAs), processors, controllers, microcontrollers, microprocessors, electronic devices, other electronic units designed to perform the functions described in the present disclosure, computer, or a combination thereof.

Accordingly, various example logic blocks, modules, and circuits described in connection with the present disclosure may be implemented or performed with general purpose processors, DSPs, ASICs, FPGAs or other programmable logic devices, discrete gate or transistor logic, discrete hardware components, or any combination of those designed to perform the functions described herein. The general purpose processor may be a microprocessor, but in the alternative, the processor may be any related processor, controller, microcontroller, or state machine. The processor may also be implemented as a combination of computing devices, for example, a DSP and microprocessor, a plurality of microprocessors, one or more microprocessors associated with a DSP core, or any other combination of the configurations.

In the implementation using firmware and/or software, the techniques may be implemented with instructions stored on a computer-readable medium, such as random access memory (RAM), read-only memory (ROM), non-volatile random access memory (NVRAM), programmable read-only memory (PROM), erasable programmable read-only memory (EPROM), electrically erasable PROM (EEPROM), flash memory, compact disc (CD), magnetic or optical data storage devices, etc. The instructions may be executable by one or more processors, and may cause the processor(s) to perform certain aspects of the functions described in the present disclosure.

When implemented in software, the techniques may be stored on a computer-readable medium as one or more instructions or codes, or may be transmitted through a computer-readable medium. The computer-readable media include both the computer storage media and the communication media including any medium that facilitates the transmission of a computer program from one place to another. The storage media may also be any available media that may be accessible to a computer. By way of non-limiting example, such a computer-readable medium may include RAM, ROM, EEPROM, CD-ROM or other optical disk storage, magnetic disk storage or other magnetic storage devices, or any other media that can be used to transmit or store desired program code in the form of instructions or data structures and can be accessible to a computer. In addition, any connection is properly referred to as a computer-readable medium.

For example, if the software is sent from a website, server, or other remote sources using coaxial cable, fiber optic cable, twisted pair, digital subscriber line (DSL), or wireless technologies such as infrared, wireless, and microwave, the coaxial cable, the fiber optic cable, the twisted pair, the digital subscriber line, or the wireless technologies such as infrared, wireless, and microwave are included within the definition of the medium. The disks and the discs used herein include CDs, laser disks, optical disks, digital versatile discs (DVDs), floppy disks, and Blu-ray disks, where disks usually magnetically reproduce data, while discs optically reproduce data using a laser. The combinations described above should also be included within the scope of the computer-readable media.

The software module may reside in RAM memory, flash memory, ROM memory, EPROM memory, EEPROM memory, registers, hard disk, removable disk, CD-ROM, or any other form of storage medium known. An exemplary storage medium may be connected to the processor such that the processor may read or write information from or to the storage medium. Alternatively, the storage medium may be integrated into the processor. The processor and the storage medium may exist in the ASIC. The ASIC may exist in the user terminal. Alternatively, the processor and storage medium may exist as separate components in the user terminal.

Although the examples described above have been described as utilizing aspects of the currently disclosed subject matter in one or more standalone computer systems, aspects are not limited thereto, and may be implemented in conjunction with any computing environment, such as a network or distributed computing environment. Furthermore, the aspects of the subject matter in the present disclosure may be implemented in multiple processing chips or apparatus, and storage may be similarly influenced across a plurality of apparatus. Such apparatus may include PCs, network servers, and portable apparatus.

Although the present disclosure has been described in connection with some examples herein, various modifications and changes can be made without departing from the scope of the present disclosure, which can be understood by those skilled in the art to which the present disclosure pertains. In addition, such modifications and changes should be considered within the scope of the claims appended herein.

The invention claimed is:

1. A method for generating three-dimensional blood vessel profile data, the method being performed by at least one processor and comprising:
- acquiring a plurality of images comprising images of blood vessels;
- generating, based on a first image of the plurality of images and a second image of the plurality of images, three-dimensional first blood vessel profile data;
- generating, based on the second image and a third image of the plurality of images, three-dimensional second blood vessel profile data;
- identifying a first coordinate value corresponding to a first point of the blood vessels, wherein the first coordinate value is associated with the three-dimensional second blood vessel profile data;
- identifying, based on the first coordinate value, a second coordinate value in the second image;
- identifying, based on the second coordinate value, a third coordinate value corresponding to the first point of the blood vessels, wherein the third coordinate value is associated with the three-dimensional first blood vessel profile data;
- acquiring three-dimensional third blood vessel profile data by merging, at least based on the third coordinate value, at least the three-dimensional first blood vessel profile data and the three-dimensional second blood vessel profile data; and
- outputting, based on the three-dimensional third blood vessel profile data, at least one image associated with the blood vessels.

2. The method according to claim 1, wherein the plurality of images comprise a plurality of angiographic images acquired at different viewing angles.

3. The method according to claim 1, wherein the first point of the blood vessels comprises a boundary point at which a value indicating a degree of identifying a specific region in the blood vessels in the third image is less than a value specified between proximal and distal portions of the blood vessels.

4. The method according to claim 1, further comprising:
- determining, based on the three-dimensional third blood vessel profile data, an estimated blood flow characteristic value of the blood vessels, and
- wherein:
- from a proximal portion of the blood vessels to the first point of the blood vessels, the estimated blood flow characteristic value corresponds to a first blood flow characteristic value estimated by using the three-dimensional second blood vessel profile data, and
- from the first point of the blood vessels to a distal portion of the blood vessels, the estimated blood flow characteristic value corresponds to a second blood flow characteristic value estimated by using the three-dimensional first blood vessel profile data and the first blood flow characteristic value as an initial value.

5. The method according to claim 1, further comprising:
- generating, based on the first image and a fourth image of the plurality of images, three-dimensional fourth blood vessel profile data;
- identifying a third-dimensional fourth coordinate value corresponding to a second point of the blood vessels, wherein the third-dimensional fourth coordinate value is associated with the three-dimensional third blood vessel profile data;

identifying, based on the third-dimensional fourth coordinate value, a two-dimensional fifth coordinate value in the first image;

identifying, based on the two-dimensional fifth coordinate value, a three-dimensional sixth coordinate value corresponding to the second point of the blood vessels, wherein the three-dimensional sixth coordinate value is associated with the three-dimensional fourth blood vessel profile data; and acquiring three-dimensional fifth blood vessel profile data by merging, at least based on the three-dimensional sixth coordinate value, at least the three-dimensional third blood vessel profile data and the three-dimensional fourth blood vessel profile data.

6. The method according to claim 5, further comprising:

generating, based on the first image and a fifth image of the plurality of images, three-dimensional sixth blood vessel profile data;

identifying a three-dimensional seventh coordinate value corresponding to a third point of the blood vessels, wherein the three-dimensional seventh coordinate value is associated with the three-dimensional sixth blood vessel profile data;

identifying, based on the three-dimensional seventh coordinate value, a two-dimensional eighth coordinate value in the first image; and identifying, based on the two-dimensional eighth coordinate value, a three-dimensional ninth coordinate value corresponding to the third point of the blood vessels, wherein the three-dimensional ninth coordinate value is associated with the three-dimensional fourth blood vessel profile data, wherein the acquiring the three-dimensional fifth blood vessel profile data comprises acquiring the three-dimensional fifth blood vessel profile data by merging, at least based on the three-dimensional sixth coordinate value and the three-dimensional ninth coordinate value, at least the three-dimensional third blood vessel profile data, the three-dimensional fourth blood vessel profile data, and the three-dimensional sixth blood vessel profile data.

7. The method according to claim 1, further comprising:

generating, based on the second image and a fourth image of the plurality of images, three-dimensional fourth blood vessel profile data;

identifying a three-dimensional fourth coordinate value corresponding to a second point of the blood vessels, wherein the three-dimensional fourth coordinate value is associated with the three-dimensional fourth blood vessel profile data;

identifying, based on the three-dimensional fourth coordinate value, a two-dimensional fifth coordinate value in the second image; and identifying, based on the two-dimensional fifth coordinate value, a three-dimensional sixth coordinate value corresponding to the second point of the blood vessels, wherein the three-dimensional sixth coordinate value is associated with the three-dimensional first blood vessel profile data, wherein the acquiring the three-dimensional third blood vessel profile data comprises acquiring the three-dimensional third blood vessel profile data by merging, at least based on the third coordinate value and the three-dimensional sixth coordinate value, at least the three-dimensional first blood vessel profile data, the three-dimensional second blood vessel profile data, and the three-dimensional fourth blood vessel profile data.

8. The method according to claim 1, further comprising:

generating, based on the first image and a fourth image of the plurality of images, three-dimensional fourth blood vessel profile data;

identifying a three-dimensional fourth coordinate value corresponding to a second point of the blood vessels, wherein the three-dimensional fourth coordinate value is associated with the three-dimensional fourth blood vessel profile data;

identifying, based on the three-dimensional fourth coordinate value, a two-dimensional fifth coordinate value in the first image; and identifying, based on the two-dimensional fifth coordinate value, a three-dimensional sixth coordinate value corresponding to the second point of the blood vessels, wherein the three-dimensional sixth coordinate value is associated with the three-dimensional first blood vessel profile data, wherein the acquiring the three-dimensional third blood vessel profile data comprises acquiring the three-dimensional third blood vessel profile data by merging, at least based on the third coordinate value and the three-dimensional sixth coordinate value, at least the three-dimensional first blood vessel profile data, the three-dimensional second blood vessel profile data, and the three-dimensional fourth blood vessel profile data.

9. An electronic device, comprising:

one or more processors; and memory storing one or more computer-readable programs, wherein the one or more computer-readable programs comprise instructions that, when executed by the one or more processors, are configured to cause the electronic device to:

acquire a plurality of images comprising images of blood vessels;

generate, based on a first image of the plurality of images and a second image of the plurality of images, three-dimensional first blood vessel profile data;

generate, based on the second image and a third image of the plurality of images, three-dimensional second blood vessel profile data;

identify a first coordinate value corresponding to a first point of the blood vessels, wherein the first coordinate value is associated with the three-dimensional second blood vessel profile data;

identify, based on the first coordinate value, a second coordinate value in the second image;

identify, based on the second coordinate value, a third coordinate value corresponding to the first point of the blood vessels, wherein the third coordinate value is associated with the three-dimensional first blood vessel profile data;

acquire three-dimensional third blood vessel profile data by merging, at least based on the third coordinate value, at least the three-dimensional first blood vessel profile data and the three-dimensional second blood vessel profile data; and output, based on the three-dimensional third blood vessel profile data, at least one image associated with the blood vessels.

10. The electronic device according to claim 9, wherein the plurality of images comprise a plurality of angiographic images acquired at different viewing angles.

11. The electronic device according to claim 9, wherein the first point of the blood vessels comprises a boundary point at which a value indicating a degree of identifying a specific region in the blood vessels in the third image is less than a value specified between proximal and distal portions of the blood vessels.

12. The electronic device according to claim 9, wherein the instructions, when executed by the one or more processors, are configured to cause the electronic device to determine, based on the three-dimensional third blood vessel profile data, an estimated blood flow characteristic value of the blood vessels, and wherein:

from a proximal portion of the blood vessels to the first point of the blood vessels, the estimated blood flow characteristic value corresponds to a first blood flow characteristic value estimated by using the three-dimensional second blood vessel profile data, and from the first point of the blood vessels to a distal portion of the blood vessels, the estimated blood flow characteristic value corresponds to a second blood flow characteristic value estimated by using the three-dimensional first blood vessel profile data and the first blood flow characteristic value as an initial value.

13. The electronic device according to claim 9, wherein the instructions, when executed by the one or more processors, are configured to cause the electronic device to:

generate, based on the first image and a fourth image of the plurality of images, three-dimensional fourth blood vessel profile data;

identify a third-dimensional fourth coordinate value corresponding to a second point of the blood vessels, wherein the third-dimensional fourth coordinate value is associated with the three-dimensional third blood vessel profile data;

identify, based on the third-dimensional fourth coordinate value, a two-dimensional fifth coordinate value in the first image;

identify, based on the two-dimensional fifth coordinate value, a three-dimensional sixth coordinate value corresponding to the second point of the blood vessels, wherein the three-dimensional sixth coordinate value is associated with the three-dimensional fourth blood vessel profile data; and acquiring three-dimensional fifth blood vessel profile data by merging, at least based on the three-dimensional sixth coordinate value, at least the three-dimensional third blood vessel profile data and the three-dimensional fourth blood vessel profile data.

14. The electronic device according to claim 13, wherein the instructions, when executed by the one or more processors, are configured to cause the electronic device to:

generate, based on the first image and a fifth image of the plurality of images, three-dimensional sixth blood vessel profile data;

identify a three-dimensional seventh coordinate value corresponding to a third point of the blood vessels, wherein the three-dimensional seventh coordinate value is associated with the three-dimensional sixth blood vessel profile data;

identify, based on the three-dimensional seventh coordinate value, a two-dimensional eighth coordinate value in the first image; and identify, based on the two-dimensional eighth coordinate value, a three-dimensional ninth coordinate value corresponding to the third point of the blood vessels, wherein the three-dimensional ninth coordinate value is associated with the three-dimensional fourth blood vessel profile data, and wherein the three-dimensional fifth blood vessel profile data is acquired by merging, at least based on the three-dimensional sixth coordinate value and the three-dimensional ninth coordinate value, at least the three-dimensional third blood vessel profile data, the three-dimensional fourth blood vessel profile data, and the three-dimensional sixth blood vessel profile data.

15. The electronic device according to claim 9, wherein the instructions, when executed by the one or more processors, are configured to cause the electronic device to:

generate, based on the second image and a fourth image of the plurality of images, three-dimensional fourth blood vessel profile data;

identify a three-dimensional fourth coordinate value corresponding to a second point of the blood vessels, wherein the three-dimensional fourth coordinate value is associated with the three-dimensional fourth blood vessel profile data;

identify, based on the three-dimensional fourth coordinate value, a two-dimensional fifth coordinate value in the second image; and identify, based on the two-dimensional fifth coordinate value, a three-dimensional sixth coordinate value corresponding to the second point of the blood vessels, wherein the three-dimensional sixth coordinate value is associated with the three-dimensional first blood vessel profile data, and wherein the three-dimensional third blood vessel profile data is acquired by merging, at least based on the third coordinate value and the three-dimensional sixth coordinate value, at least the three-dimensional first blood vessel profile data, the three-dimensional second blood vessel profile data, and the three-dimensional fourth blood vessel profile data.

16. The electronic device according to claim 9, wherein the instructions, when executed by the one or more processors, are configured to cause the electronic device to:

generate, based on the first image and a fourth image of the plurality of images, three-dimensional fourth blood vessel profile data;

identify a three-dimensional fourth coordinate value corresponding to a second point of the blood vessels, wherein the three-dimensional fourth coordinate value is associated with the three-dimensional fourth blood vessel profile data;

identify, based on the three-dimensional fourth coordinate value, a two-dimensional fifth coordinate value in the first image; and identify, based on the two-dimensional fifth coordinate value, a three-dimensional sixth coordinate value corresponding to the second point of the blood vessels, wherein the three-dimensional sixth coordinate value is associated with the three-dimensional first blood vessel profile data, and wherein the three-dimensional third blood vessel profile data is acquired by merging, at least based on the third coordinate value and the three-dimensional sixth coordinate value, at least the three-dimensional first blood vessel profile data, the three-dimensional second blood vessel profile data, and the three-dimensional fourth blood vessel profile data.

17. A non-transitory computer-readable recording medium storing instructions that, when executed by at least one processor, cause a computing device to:

acquire a plurality of images comprising images of blood vessels;

generate, based on a first image of the plurality of images and a second image of the plurality of images, three-dimensional first blood vessel profile data;

generate, based on the second image and a third image of the plurality of images, three-dimensional second blood vessel profile data;

identify a first coordinate value corresponding to a first point of the blood vessels, wherein the first coordinate value is associated with the three-dimensional second blood vessel profile data;

identify, based on the first coordinate value, a second coordinate value in the second image;

identify, based on the second coordinate value, a third coordinate value corresponding to the first point of the blood vessels, wherein the third coordinate value is associated with the three-dimensional first blood vessel profile data;

acquire three-dimensional third blood vessel profile data by merging, at least based on the third coordinate value, at least the three-dimensional first blood vessel profile data and the three-dimensional second blood vessel profile data; and output, based on the three-dimensional third blood vessel profile data, at least one image associated with the blood vessels.

* * * * *